United States Patent
Sankaranarayanan

(12) 
(10) Patent No.: US 6,608,094 B2
(45) Date of Patent: Aug. 19, 2003

(54) COMPOUNDS FOR THE MANAGEMENT OF AGING-RELATED AND DIABETIC VASCULAR COMPLICATIONS, PROCESS FOR THEIR PREPARATION AND THERAPEUTIC USES THEREOF

(75) Inventor: Alangudi Sankaranarayanan, Ahmedabad (IN)

(73) Assignee: Torrent Pharmaceuticals Ltd., Gujarat (IN)

( * ) Notice: Subject to any disclaimer, the term of this patent is extended or adjusted under 35 U.S.C. 154(b) by 0 days.

(21) Appl. No.: 09/939,702

(22) Filed: Aug. 28, 2001

(65) Prior Publication Data

US 2003/0032660 A1 Feb. 13, 2003

Related U.S. Application Data

(63) Continuation-in-part of application No. 09/801,778, filed on Mar. 9, 2001, now abandoned, which is a continuation-in-part of application No. 09/598,410, filed on Jun. 21, 2000, now Pat. No. 6,462,057, which is a continuation-in-part of application No. PCT/IB99/01683, filed on Oct. 15, 1999.

(30) Foreign Application Priority Data

Oct. 6, 1999 (IN) ................................................. 828/99

(51) Int. Cl.[7] ................ A61K 31/4436; A61K 31/4425; C07D 409/06; C07D 213/20
(52) U.S. Cl. .................... 514/358; 546/280.4; 546/324; 546/347; 514/336; 514/354; 514/356; 514/358
(58) Field of Search .............................. 546/347, 280.4, 546/324, 336, 354, 356; 514/358

(56) References Cited

U.S. PATENT DOCUMENTS 5,853,703 A 12/1998 Cerami et al. ................ 424/53

FOREIGN PATENT DOCUMENTS

GB 822351 A 10/1959

OTHER PUBLICATIONS

Binenfeld, Zlatko et al, Acta Pharm. Jugosl 1981, 31 (1), 5–15.*
Beisswenger et al, *Diabetes*, 11:824–829 (1995).
Beisswenger et al, *J. Clin. Invest.*, 92:212–217 (1993).
Anderson et al, *J. Clin. Invest.*, 92:3045–3052 (1993).
Makita et al, *New England J. of Med.*, 325(12):836–842 (1991).
Yamauchi et al, *Diabetes Res. Clin. Pract.*, 34(3):127–133 (1997) (Abstract only).
Ellis et al, *Metabolism*, 40(10):1016–1019 (1991) (Abstract only).
Nakamura et al, *Diabetes*, 46(5):895–899 (1997).
Soulis–Liparota et al, *Diabetes*, 40:1328–1334 (1991).
Chibber et al, *Diabetologia*, 40(2):156–164 (1997).

Hirata et al, *Biochem. Biophys. Res. Commun.*, 236(3):712–715 (1997).
Murata et al, *Diabetologia*, 40(7):764–769 (1997).
Clements Jr. et al, *J. Diabetes Complication*, 12(1):28–33 (1998) (Abstract only).
Hammes et al, *Proc. Natl. Acad. Sci. USA*, 88:11555–11558 (1991) (with 1 page correction).
Hammes et al, *Diabetologia*, 37(1):32–35 (1994).
Roufail et al, *Diabetologia*, 41(12):1419–1425 (1998).
Kihara et al, *Proc. Natl. Acad. Sci. USA*, 88:6107–6111 (1991).
Miyauchi et al, *Eur. J. Endocrinol.*, 134(4):467–473 (1996) (Abstract only).
Yagihashi et al, *Diabetes*, 41:47–52 (1992).
Ritthaler et al, *Nephrol Dial Transplant*, 10(9):1662–1667 (1995).
Amore et al, *Kidney International*, 51;27–35 (1997).
Bierhaus et al, *Circulation*, 96(7):2262–2271 (1997).
Bierhaus et al, *Diabetes*, 46:1481–1490 (1997).
Kunt et al, *Exp. Clin. Endocrinol Diabetes*, 106:183–188 (1998).
Kunt et al, *Int. J. Mol. Med.*, 2(4):455–460 (1998) (Abstract only).
Vlassara et al, *Molecular Medicine*, 1(4):447–456 (1995).
Kyurkchiev et al, *Cell Mol Life Sci.*, 53(11–12):911–916 (1997) (Abstract only).

(List continued on next page.)

*Primary Examiner*—Alan L. Rotman
*Assistant Examiner*—Janet L Coppins
(74) *Attorney, Agent, or Firm*—Sughrue Mion, PLLC

(57) ABSTRACT

Novel compounds of the pyridinium series useful for the management of diabetes and aging-related vascular and neurovascular complications, including kidney disease, nerve damage, atherosclerosis, retinopathy, inflammatory disorders, immunological disorders, oxidative stress, dermatological disorders and discoloration of teeth, by breaking preformed AGE, of the general formula I, or pharmaceutically acceptable salts thereof,

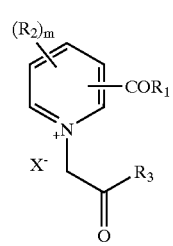

(I)

wherein, $R_1$, $R_2$, $R_3$, X and m are as defined in the specification. Also disclosed is a method for preparation of the compounds of general formula (I) and pharmaceutical composition containing one or more compounds as defined above as active ingredients. Also disclosed is a method of treatment of a diabetic patient by administering the compounds as defined above, either singly or in combination with drugs for antidiabetic therapy.

41 Claims, No Drawings

OTHER PUBLICATIONS

Yamagishi et al, *Diabetologia,* 41(12):1435–1441 (1998).
Hogan et al, *J. Clin. Invest.,* 90(3):1110–1115 (1992).
Tezuka et al, *Biochem Biophys. Res. Commun.,* 193(2):674–680 (1993) (Abstract only).
Bonnardel et al, *Diabetes,* 48:2052–2058 (1999).
Vlassara et al, *Proc. Natl. Acad. Sci., USA,* 89:12043–12047 (1992).
Bucala, *Diabetes Res. Clin. Pract.,* 30(Suppl):123–130 (1996) (Abstract only).
Kirstein et al, *Proc. Natl. Acad. Sci., USA,* 87:9010–9014 (1990).
Wolffenbuttel et al, *Proc. Natl. Acad. Sci., USA,* 95:4630–4634 (1998).
Aronson et al, *J. Am. Coll Cardiol.,* 27(3):528–535 (1996) (Abstract only).
Seftel et al, *Urology,* 50(6):1016–1026 (1997) (Abstract only).
Vitek et al, *Proc. Natl. Acad. Sci., USA,* 91:4766–4770 (1994).
Li et al, *Proc. Natl. Acad. Sci., USA,* 93:3902–3907 (1996).
Nordbo, *J. Dent. Res.,* 58(4):1429 (1979) (Abstract only).
Nakayama et al, *Biochem. Biophys. Res. Comm.,* 162(2):740–745 (1989).
Araki et al, *J. Biol. Chem.,* 267(15):10211–10214 (1992).
Horiuchi et al, *J. Biol. Chem.,* 266(12):7329–7331 (1991).
Booth et al, *Biochem. Biophys. Res. Comm.,* 220(Art. No. 0366):113–119 (1996).
Brownlee, *Annu. Review Med.,* 46:223–234 (1995).
Shikata et al, *J. Diabetes Complic.,* 9(4):296–271 (1995).
International Preliminary Examination Report for PCT/IB99/01683 dated Dec. 21, 2001.
Complete Chinese Language Reference of Kao Yee–Shang et al, Chemical Abstracts vol. 52, No. 3, 1958.
Kenichi Shikata et al, Journal of Diabetes and its complications 1995:9: 269–271.
Sara Vasan et al, Nature, vol. 382, Jul. 18, 1996, 275–278.
M.Brownlee et al Science Jun. 1986, 232: 1629–32.
A Ceriello, Diab. Nutr. Metab.12: 42–46, 1999.
Horiuchi S et al, The Journal of Biological Chemistry 1991,266:7329–7332.
Wolffenbuttel, B.H.R et al, Proc.Natl. Acad.Sci, USA, Apr. 1998: 4630–4634.
Mohammed Asif et al, PNAS Mar. 14, 2000, vol. 97, No. 6, 2809–2813.
Raj D S et al, Am J Kidney Dis Mar. 2000 35(3): 365–80.
J.Shashi et al, Indian drugs 1995, 32(7) pp. 317–319 (XP 000909803).
Tiwari, S.S. et al, J. Indian Chem Soc, 1975, 52(2), 166–7 (XP 000909760).
Mocanu, G. et al, S.T.P. Pharma Sciences 1994, 4(4) 287–291 (XP 000909810).
Sarel, Shalom et al, J.med. Chem. 1999, 42(2) 242–248 (XP 000910109).
Demchenko, A.M. et al, Chemistry of Hetcrocyclic compounds 1997, 33(10), 1191–1195 (XP 000909851).
Onedera, Akira et al, Chemical Abstracts, vol. 120, No. 8, Feb. 21, 1994, abstract No. 90688 (XP 002139440).
Pandey V.K. et al, Indian Drugs, 1983, 20(12),492–4 (XP 000909902).
Maksimovic, Matez et al, Chemical Abstracts vol. 96 No. 13, Mar. 29, 1982 abstract No. 99045 (XP 002139441).
Binenfeld, Zlatko et al, Acta Pharm. Jugosl 1981, 31(1), 5–15 (XP 000909901).
Ergenc, Nedime Chemical Abstracts vol. 65, No. 6, Sep. 12, 1996, abstract No. 8891f (XP 002139442).
Kao, Yee–Shang et al, Chemical Abstracts vol. 52, No. 3, 1958 abstract No. 12860f (XP 002139443).
PCT Search report of Corresponding PCT application No. PCT/IB99/01683 dated Jul. 10, 2000.

\* cited by examiner

COMPOUNDS FOR THE MANAGEMENT OF AGING-RELATED AND DIABETIC VASCULAR COMPLICATIONS, PROCESS FOR THEIR PREPARATION AND THERAPEUTIC USES THEREOF

This is a continuation-in-part application of application Ser. No. 09/801,778 filed Mar. 9, 2001, abandoned, which is a continuation-in-part application of application Ser. No. 09/598,410 filed Jun. 21, 2000, issued as U.S. Pat. No. 6,462,057, which is a continuation-in-part application of International Application No. PCT/IB99/01683 filed on Oct. 15, 1999, the disclosures of which are incorporated herein by reference, which International Application has been published by the International Bureau in English on Apr. 12, 2001.

BACKGROUND OF THE INVENTION

1. Field of the Invention

The present invention relates to a new class of compounds of pyridinium series and to their use in treatment of diabetes and related illnesses. More particularly the invention relates to compounds of this series, methods for their preparation, pharmaceutical composition containing these compounds and their use in the treatment of complications of diabetes mellitus. The compounds of this series exhibit AGE breaking and inhibiting activity, which is essential for the treatment of diabetic and aging-related vascular and neurovascular complications including kidney disease, nerve damage, atherosclerosis, retinopathy, inflammatory disorders, immunological disorders, oxidative stress and dermatological conditions. The invention also extends to the method of reversing the discoloration of teeth resulting from nonenzymatic browning in the oral cavity which comprises administration of an amount effective to reverse pre-formed advanced glycosylation crosslinks.

2. Description of the Related Art

Maillard in 1912 found that reducing sugars, such as glucose and ribose react with proteins to form brown pigments. Further studies have shown that this is an irreversible non-enzymatic reaction, which occurs in several natural systems including stored foodstuff. Maillard reaction occurs in two stages, early and advanced. Initially, proteins react with glucose to form stable Amadori products, which subsequently crosslinks to form advanced glycation end products (AGE). In most cases, the formation of AGE also accompanies browning of the proteins and increase in the fluorescence.

In diabetes, where blood glucose level is significantly higher than normal, the reaction of glucose with several proteins such as haemoglobin, lens crystallin and collagen, gives rise to the formation of AGE, which in turn, is responsible for the complications associated with diabetes, such as nephropathy, microangiopathy, endothelial dysfunction and other organ dysfunctions. In addition, the activity of several growth factors, such as basic fibroblast growth factor, is also impaired. AGE products, unlike normal proteins in tissue, have a slower rate of turnover and replenishment. It has been reported that AGE products may in fact elicit a complex immunological reaction involving RAGE (Receptor for Advanced Glycation End Products) receptors and activation of several incompletely defined immunological processes. It has been documented that diabetes with evidence of microangiopathy and macroangiopathy also show evidence of oxidative stress, the mechanism of which has not been elucidated.

In vitro AGE formation can be studied in the laboratory by incubating reducing sugars, such as ribose or glucose with bovine serum albumin. AGE formation can be detected by increase in the fluorescence or increased cross reactivity with anti-AGE antibodies. The increase in fluorescence seems to precede formation of AGE specific antigenic epitopes. This increase in fluorescence is used to monitor the increased AGE formation in vitro (Brownlee M et al, Science 1986; 232:1629–1632). In addition to the increase in the fluorescence, one of the most important features of in vitro AGE formation is the formation of antigenic epitopes that are specific to AGE and not to the native proteins. Therefore, it is possible to raise antibodies against advanced glycation end products of one protein and use them to detect AGE formation in other proteins. This has served as an important analytical tool in AGE research.

Due to the clinical significance of AGE formation, many approaches are being used to diagnose, prevent, or revert AGE formation in the body. The formation of AGE could be inhibited by reacting with an early glycosylation product that results from the original reaction between the target protein and glucose. The inhibition was believed to take place as the reaction between the inhibitor and the early glycosylation product appeared to interrupt the subsequent reaction of the glycosylated protein with additional protein material to form the cross linked late stage product. Compounds like aminoguanidine act to inhibit AGE formation by such mechanism.

The formation of AGE on long-lived proteins is also associated with cross-linking of these proteins. The AGE derived protein cross-links have been shown to be cleaved by compounds like N-phenacyl thiazolium bromide (PTB), which reacts with and cleaves covalent, AGE derived protein cross links (Vasan et al. Nature 1996; 382: 275–278; U.S. Pat. No. 5,853,703, Date of Patent: Dec. 29, 1998). The mechanism of reducing the AGE content in tissues is expected to take place relatively rapidly, in contrast to aminoguanidine, which acts slowly by its very nature of mechanism of action. This current specification is related to compounds of pyridinium class, which break pre-formed AGE, like PTB, and in some cases even more effectively by than PTB.

SUMMARY OF THE INVENTION

The main objective of the present invention is to provide a new class of compounds of the pyridinium series which are useful for the management of diabetes and aging related vascular and neurovascular complications and particularly in the treatment of complications of diabetes mellitus and other aging related conditions including kidney disease, nerve damage, atherosclerosis, retinopathy, inflammatory disorders, immunological disorders, oxidative stress and dermatological conditions. The invention also extends the method to reverse the discoloration of teeth resulting from nonenzymatic browning in the oral cavity which comprises administration of an amount effective to reverse the pre-formed advanced glycosylation crosslinks, etc.

Another object of the present invention is to provide compounds of the pyridinium series, which exhibit AGE breaking activities.

Yet another object of the present invention is to provide a method of preparation of compounds of the pyridinium series which exhibit AGE breaking activities.

Still another object of the invention is to provide pharmaceutical compositions with a new class of compounds of the pyridinium series according to the invention and their pharmaceutically acceptable salts in combination with suitable carriers, solvents, excepients, diluents and other media normally employed in preparing such compositions.

Still another object of the invention is to provide a method of treatment of a diabetic patient by administration of the compounds of the invention, either singly or in combination with drugs for anti-diabetic therapy, or pharmaceutically acceptable salts thereof in required dosage in admixture with pharmaceutically acceptable diluent, solvent, excepients, carriers or other media as may be appropriate for the purpose.

DETAILED DESCRIPTION OF THE INVENTION

The present invention provides for a new class of AGE breakers, of general formula I,

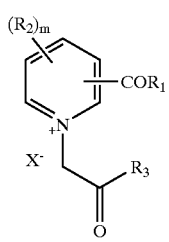

(I)

wherein $R_1$ is —$R_4$—$R_5$ or —N($R_7$) N ($R_7$) $R_9$;

$R_4$ is selected from the group consisting of —N($R_7$) $R_6$O—, —N($R_7$)$R_6$N($R_7$)—, —O$R_6$O—, and —O$R_6$N ($R_7$)—, where $R_6$ is alkyl with $C_2$ to $C_8$ carbon atoms;

$R_5$ is selected from the group consisting of alkyl, aryl including heteroaryl, —CO$R_7$, —SO$_2R_7$, —C(S)NHR$_7$, —C(NH)NHR$_7$, —COR$_{10}$,

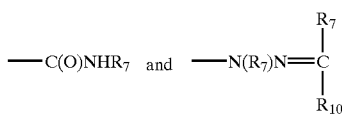

where $R_7$ is selected from the group consisting of H, alkyl and aryl including heteroaryl provided $R_7$ may be the same or different for $R_1$ and $R_3$ in the same compound;

$R_2$ is selected from the group consisting of F, Cl, Br, I, OR$_7$, NO$_2$, alkyl, aryl including heteroaryl, formyl, acyl, C(O)NR$_7R_{10}$, C(O)OR$_7$, NR$_7R_{10}$, N=C(R$_7$) (R$_{10}$), SR$_7$, SO$_2$NH$_2$, SO$_2$alkyl and SO$_2$aryl, and m is 0, 1 or 2;

$R_3$ is selected from the group consisting of $R_7$, OR$_7$, N(R$_7$)(R$_{10}$), N=C(R$_7$)(R$_{10}$), N(R$_7$)N(R$_7$)(R$_{10}$), N(R$_7$)N=C(R$_7$)(R$_{10}$) and CH(R$_7$)C(O)R$_8$ where $R_8$ is selected from the group consisting of $R_7$, OR$_7$ and NR$_7R_{10}$;

$R_9$ is selected from the group consisting of hydrogen, alkyl, aryl including heteroaryl, —C(O)R$_{10}$, —SO$_2R_{10}$, —C(S)NHR$_{10}$, —C(NH)NH(R$_{10}$) and —C(O)NHR$_{10}$;

$R_{10}$ is selected for the group consisting of H, alkyl or aryl including heteroaryl and in each case may be the same or different from substituent $R_7$, provided $R_{10}$ may be the same or different for $R_1$ and $R_3$ in the same compound;

X is selected from group consisting of a halide ion, acetate ion, perchlorate ion, sulfonate ion, oxalate ion, citrate ion, tosylate ion, maleate ion, mesylate ion, carbonate ion, sulfite ion, phosphoric hydrogen ion, phosphonate ion, phosphate ion, BF$_4^-$ and PF$_6^-$; with proviso that,
(i) when two alkyl groups are present on the same carbon or nitrogen, they may be linked together to form a cyclic structure and
(ii) the nitrogen of heteroaryl ring of $R_{10}$, when present, may be quaternized with compound such as X—CH$_2$C(O)—R$_3$.

In a preferred embodiment, (iii) $R_3$ is OR$_7$ and $R_1$ is —NHNH$_2$ then $R_7$ is not alkyl, and (iv) when $R_3$ is OR$_7$, $R_1$ is N(R$_7$)(NR$_7$)R$_9$ and $R_9$ is C(O)R$_{10}$ where $R_{10}$ is alkyl, then $R_7$ is not hydrogen.

As used herein, "alkyl" refers to an optionally substituted hydrocarbon group joined by single carbon-carbon bonds and having 1 to 8 carbon atoms joined together. The alkyl hydrocarbon group may be linear, branched or cyclic, saturated or unsaturated. The substituents are selected from F, Cl, Br, I, N, S, O and aryl. Preferably, no more than three substituents are present.

As used herein "aryl" refers to an optionally substituted aromatic group with at least one ring having a conjugated pi-electron system, containing up to two conjugated or fused ring systems. Aryl includes carbocyclic aryl, heterocyclic aryl and biaryl groups, all of which may be optionally substituted. The substituents are selected from F, Cl, Br, I, N, O, S and straight chain or branched $C_1$–$C_6$ hydrocarbon. The substituents for the aryl group are preferably selected from F, Cl, Br, I, N, O and straight chain or branched $C_1$–$C_6$ hydrocarbon.

The novel compounds of the invention of general formula I having m as 0 or 1 and —COR$_1$ at position 3 are listed in Table 1A and the novel compounds of the invention of general formula I having m as 0 and —COR$_1$ at position 4 are listed in Table 1B. The following compounds suggested are by way of example alone of the representative compounds of the general formula I as defined above and in no way restrict the invention:

Pyridinium, 3,3'-(hydrazodicarbonyl)bis[1-(2-oxo-2-phenylethyl)-, dibromide (Compound No. 1)
Pyridinium, 3,3'-(hydrazodicarbonyl)bis[1-(2-ethoxy-2-oxoethyl)-, dibromide (Compound No.2)
Pyridinium, 3,3'-(hydrazodicarbonyl)bis[1-[2-(2,4-dichlorophenyl)-2-oxoethyl]-, dibromide (Compound No.3)
Pyridinium, 1-(2-ethoxy-2-oxoethyl)-3-[[2-(2-pyridinyl)hydrazino]carbonyl]-, bromide (Compound No.4)
Pyridinium, 3-[[2-(methylsulfonyl)hydrazino]carbonyl]-1-[2-oxo-2-(2-thienyl)ethyl]-, bromide (Compound No.5)
Pyridinium, 3,3'-(hydrazodicarbonyl)bis[1-[2-oxo-2-(2-thienyl)ethyl]-, dibromide (Compound No.6)
Pyridinium, 3-[[[2-(benzoyloxy)ethyl]amino]carbonyl]-1-(2-ethoxy-2-oxoethyl)-, bromide (Compound No.7)
Pyridinium, 3-[[[2-(benzoyloxy)ethyl]amino]carbonyl]-1-[2-(2,4-dichlorophenyl)-2-oxoethyl]-, bromide (Compound No.8)
Pyridinium, 1-[2-oxo-2-(2-thienyl)ethyl]-3-[[2-(2-pyridinyl)hydrazino]carbonyl]-, bromide (Compound No.9)
Pyridinium, 1-(2-oxo-2-phenylethyl)-3-[[2-(2-pyridinyl)hydrazino]carbonyl]-, bromide (Compound No.10)
Pyridinium, 3-(hydrazinocarbonyl)-1-(2-oxo-2-phenylethyl)-, bromide (Compound No. 11)

Pyridinium, 3-[[2-(methylsulfonyl)hydrazino]carbonyl]-1-(2-oxo-2-phenylethyl)-, bromide (Compound No.12)

Pyridinium, 1-(2-ethoxy-2-oxoethyl)-3-[[2-(methylsulfonyl)hydrazino]carbonyl]-, bromide (Compound No.13)

Pyridinium, 1-(2-oxo-2-phenylethyl)-3-[[2-(phenylsulfonyl)hydrazino]carbonyl]-, bromide (Compound No.14)

Pyridinium, 2-chloro-1-(2-oxo-2-phenylethyl)-3-[[2-(phenylsulfonyl)hydrazino]carbonyl]-, bromide (Compound No.15)

Pyridinium, 3-[[2-(acetyloxy)ethoxy]carbonyl]-1-(2-oxo-2-phenylethyl)-, bromide (Compound No.16)

Pyridinium, 3-[[2-(benzoyloxy)ethoxy]carbonyl]-1-(2-ethoxy-2-oxoethyl)-, bromide (Compound No.17)

Pyridinium, 4-[[[2-(benzoyloxy)ethyl]amino]carbonyl]-1-[2-oxo-2-(2-thienyl)ethyl]-, bromide (Compound No.18)

Pyridinium, 1-(2-ethoxy-2-oxoethyl)-4-[[2-(phenylsulfonyl)hydrazino]carbonyl]-, bromide (Compound No. 19)

Pyridinium, 1-[2-oxo-2-(phenylamino)ethyl]-4-[[2-(phenylsulfonyl)hydrazino]carbonyl]-, bromide (Compound No.20)

Pyridinium, 1-(2-ethoxy-2-oxoethyl)-3-[[2-(phenlysulfonyl)hydrazino]carbonyl]-, bromide (Compound No.21)

Pyridinium, 1-[2-(2,4-dichlorophenyl)-2-oxoethyl]-3-[(2-methoxyethoxy)carbonyl]-, bromide (Compound No.22)

Pyridinium, 3-[[[2-(benzoyloxy)ethyl]amino]carbonyl]-1-[2-oxo-2-(phenylamino)ethyl]-, chloride (Compound No.23)

Pyridinium, 1-[2-oxo-2-(2-thienyl)ethyl]-3-[[2-[(phenylamino)carbonyl]hydrazino]carbonyl]-, bromide (Compound No.24)

Pyridinium, 3-[[[2-(acetyloxy)ethyl]amino]carbonyl-1-(2-oxo-2-phenylethyl)-, bromide (Compound No.25)

Pyridinium, 1-[2-oxo-2-(phenylamino)ethyl]-3-[[2-(phenylsulfonyl)hydrazino]carbonyl]-, chloride (Compound No.26)

Pyridinium, 3-[[2-[(4-methylphenyl)sulfonyl]hydrazino]carbonyl]-1-[2-oxo-2-(phenylamino)ethyl]-, chloride (Compound No.27)

Pyridinium, 3-[[2-(benzoyloxy)ethoxy]carbonyl]-1-(2-oxo-2-phenylethyl)-, bromide (Compound No.28)

Pyridinium, 3-[(2-benzoylhydrazino)carbonyl]-1-[2-oxo-2-(2-thienyl)ethyl]-, bromide (Compound No.29)

Pyridinium, 1-(2-ethoxy-2-oxoethyl)-3-[[2-[(phenylmethyl)sulfonyl]hydrazino]carbonyl]-, bromide (Compound No.30)

Pyridinium, 1-(2-oxo-2-phenylethyl)-3-[[2-[(phenylmethyl)sulfonyl]hydrazino]carbonyl-, bromide (Compound No.31)

Pyridinium, 3,3'-(hydrazodicarbonyl)bis[1-[2-(2-furanyl)-2-oxoethyl]-, dibromide (Compound No. 32)

Pyridinium, 3,3'-(hydrazodicarbonyl)bis[1-[2-(2-thienyl)-2-oxoethyl]-, dichloride (Compound No. 33)

Pyridinium, 3-[[2-(3-cyclohexyl-1-oxopropyl)hydrazino]carbonyl]-1-[2-oxo-2-(2-thienyl)ethyl]-, bromide (Compound No. 34)

Pyridinium, 3-[[2-(3-cyclohexyl-1-oxopropyl)hydrazino]carbonyl]-1-[2-oxo-2-(phenylamino)ethyl]-, chloride (Compound No. 35)

Pyridinium, 3-[[[2-(benzoyloxy)ethyl]amino]carbonyl]-1-[2-oxo-2-(2-thienyl)ethyl]-, bromide (Compound No. 36)

Pyridinium, 3-[[[2-(benzoyloxy)ethyl]amino]carbonyl]-1-(4-ethoxy-2,4-dioxobutyl)-, chloride (Compound No. 37)

Pyridinium, 3-[[(2-methoxyethyl)amino]carbonyl]-1-[2-(2,4-dichlorophenyl)-2-oxoethyl]-, bromide (Compound No. 38)

Pyridinium, 3,3'-(hydrazodicarbonyl)bis[1-[2-(cyclopropylamino)-2-oxoethyl]-, dichloride (Compound No. 39)

Pyridinium, 1-[2-(cyclopropylamino)-2-oxoethyl]-3-[[(2-methoxyethyl)amino]carbonyl]-, chloride (Compound No. 40)

Pyridinium, 3,3'-(hydrazodicarbonyl)bis[1-[2-[(1-methylethyl)amino]-2-oxoethyl]-, dichloride (Compound No. 41)

Pyridinium, 3-[[2-[(2-chloro-3-pyridinyl)carbonyl]hydrazino]carbonyl]-1-[2-oxo-2-(2-thienyl)ethyl]-, chloride (Compound No. 42)

Pyridinium, 1-[2-[(1-methylethyl)amino]-2-oxoethyl]-3-[[2-(methylsulfonyl)hydrazino]carbonyl]-, chloride (Compound No. 43)

Pyridinium, 3-[[2-(methylsulfonyl)hydrazino]carbonyl]-1-[2-oxo-2-(1-pyrrolidinyl)ethyl]-, chloride (Compound No. 44)

Pyridinium, 3-[[2-(methylsulfonyl)hydrazino]carbonyl]-1-[2-oxo-2-(2-thienyl)ethyl]-, chloride (Compound No. 45)

Pyridinium, 3,3'-(hydrazodicarbonyl)bis[1-(carboxymethyl)-, dichloride (Compound No. 46)

Pyridinium, 3-bromo-5-[[2-methoxyethyl)amino]carbonyl]-1-[2-oxo-2-(2-thienyl)ethyl]-, chloride (Compound No. 47)

Pyridinium, 3-[[2-[[6-(methoxycarbonyl)-3-pyridinyl]carbonyl]hydrazino]carbonyl]-1-[2-oxo-2-(2-thienyl)ethyl]-, chloride (Compound No. 48)

Pyridinium, 2-methyl-1-(2-oxo-2-thien-2-yl-ethyl)-5-[[2-[[1-(2-oxo-2-thien-2-yl-ethyl)pyridinium-3-yl]carbonyl]hydrazino]carbonyl]-, dichloride (Compound No. 49)

Pyridinium, 3-[[2-[(1-methylethyl)sulfonyl]hydrazino]carbonyl]-1-[2-oxo-2-(2-thienyl)ethyl]-, bromide (Compound No. 50)

Pyridinium, 3-[[2-(methylsulfonyl)hydrazino]carbonyl]-1-[2-oxo-2-[4-(phenylmethyl)-1-piperidinyl]ethyl]-, chloride (Compound No. 51)

Pyridinium, 1-[2-[2-(ethoxycarbonyl)-1-pyrrolidinyl]-2-oxoethyl]-3-[[2-(methylsulfonyl)hydrazino]carbonyl]-, chloride (Compound No. 52)

Pyridinium, 3-bromo-5-[[2-(methylsulfonyl)hydrazino]carbonyl]-1-[2-oxo-2-(2-thienyl)ethyl]-, bromide (Compound No. 53)

Pyridinium, 3-[[2-(ethoxycarbonyl)hydrazino]carbonyl]-1-[2-oxo-2-(2-thienyl)ethyl]-, bromide (Compound No. 54)

Pyridinium, 1-[2-(5-chloro-2-thienyl)-2-oxoethyl]-3-[[2-(methylsulfonyl)hydrazino]carbonyl]-, bromide (Compound No. 55)

Pyridinium, 3,3'-(hydrazodicarbonyl)bis[1-[2-(4-nitro-2-thienyl)-2-oxoethyl]-, dichloride (Compound No. 56)

Pyridinium, 2-methyl-5-[[2-(methylsulfonyl)hydrazino]carbonyl]-1-[2-oxo-2-(2-thienyl)ethyl]-, bromide (Compound No. 57)

Pyridinium, 3,3'-(hydrazodicarbonyl)bis[1-[2-(5-methyl-2-thienyl)-2-oxoethyl]-, dichloride (Compound No. 58)

Pyridinium, 3,3'-(hydrazodicarbonyl)bis[1-[2-[2-(ethoxycarbonyl)-1-pyrrolidinyl]-2-oxoethyl]-, dichloride (Compound No. 59)

Pyridinium, 3-(aminocarbonyl)-1-(2-oxo-2-thien-2-yl-ethyl)--5-[[2-[[1-(2-oxo-2-thien-2-yl-ethyl)pyridinium-3-yl]carbonyl]hydrazino]carbonyl]-, dichloride (Compound No. 60)

Pyridinium, 1-[2-[4-(ethoxycarbonyl)-3-thiazolidinyl]-2-oxoethyl]-3-[[2-(methylsulfonyl)hydrazino]carbonyl]-, chloride (Compound No. 61)

Pyridinium, 3,3'-(hydrazodicarbonyl)bis[1-[2-(5-chloro-2-thienyl)-2-oxoethyl]-, dichloride (Compound No. 62)

Pyridinium, 3-[[2-(methylsulfonyl)hydrazino]carbonyl]-1-[2-(5-methyl-2-thienyl)-2-oxoethyl]-, chloride (Compound No. 63)

Pyridinium, 3-[[2-(methylsulfonyl)hydrazino]carbonyl]-1-[2-(4-nitro-2-thienyl)-2-oxoethyl]-, bromide (Compound No. 64)

Pyridinium, 1-[2-oxo-2-(phenylamino)ethyl]-3-[(2-phenylhydrazino)carbonyl]-, chloride(Compound No. 65)

Pyridinium, 4-[[[2-(benzoyloxy)ethyl]amino]carbonyl]-1-[2-oxo-2-(phenylamino)ethyl]-, chloride (Compound No. 66)

Pyridinium, 3-[[2-(methylsulfonyl)hydrazino]carbonyl]-1-[2-(5-nitro-2-thienyl)-2-oxoethyl]-, chloride (Compound No. 67)

Pyridinium, 1-[2-oxo-2-(2-thienyl)ethyl]-3-[[2-[(trifluoromethyl)sulfonyl]hydrazino]carbonyl]-, bromide (Compound No. 68)

Pyridinium, 1-[2-oxo-2-(2-thienyl)ethyl]-3-[(2-phenylhydrazino)carbonyl]-, bromide (Compound No. 69)

Pyridinium, 3-[[2-[(4-methoxyphenyl)sulfonyl]hydrazino]carbonyl]-1-[2-oxo-2-(2-thienyl)ethyl]-, bromide (Compound No. 70)

Pyridinium, 1-(2-ethoxy-2-oxoethyl)-3-[[2-[(phenylamino)carbonyl]hydrazino]carbonyl]-, bromide (Compound No. 71)

Pyridinium, 1-(2-ethoxy-2-oxoethyl)-3-[[2-[(4-methylphenyl)sulfonyl]hydrazino]carbonyl]-, bromide (Compound No. 72)

Pyridinium, 1-(2-oxo-2-phenylethyl)-3-[[2-[(phenylamino)carbonyl]hydrazino]carbonyl]-, bromide (Compound No.73)

Pyridinium, 1-[2-oxo-2-(phenylamino)ethyl]-3-[[2-[(phenylmethyl)sulfonyl]hydrazino]carbonyl]-, chloride (Compound No. 74)

Pyridinium, 4-[[2-(methylsulfonyl)hydrazino]carbonyl]-1-(2-oxo-2-phenylethyl)-, bromide (Compound No. 75)

Pyridinium, 1-(2-oxo-2-phenylethyl)-3-[(2-phenylhydrazino)carbonyl]-, bromide (Compound No. 76)

Pyridinium, 4-[[[2-(benzoyloxy)ethyl]amino]carbonyl]-1-(2-ethoxy-2-oxoethyl)-, bromide (Compound No. 77)

Pyridinium, 1-(2-ethoxy-2-oxoethyl)-3-[(2-phenylhydrazino)carbonyl]-, bromide (Compound No. 78)

Pyridinium, 3-[[2-[(4-methoxyphenyl)sulfonyl]hydrazino]carbonyl]-1-(2-oxo-2-phenylethyl)-, bromide (Compound No. 79)

Pyridinium, 4-[[[2-(benzoyloxy)ethyl]amino]carbonyl]-1-(2-oxo-2-phenylethyl)-, bromide (Compound No. 80)

Pyridinium, 1-(2-ethoxy-2-oxoethyl)-4-[[2-(methylsulfonyl)hydrazino]carbonyl]-, bromide (Compound No. 81)

In place of specific halide salts of the compounds listed above, these compounds may also be in the form of other pharmaceutically acceptable salts falling within the definition of X as given above. The words "and pharmaceutically acceptable salts thereof" as used herein following the names of specific compounds of general formula (I) of the invention means that such compounds encompass other pharmaceutically acceptable salts falling within. the definition of X.

TABLE 1A

Representative Pyridinium derivatives
(having m as 0 or 1 and —COR$_1$ at position 3)

| Compound | R$_1$ | —R$_2$ | —R$_3$ | —X |
|---|---|---|---|---|

TABLE 1A-continued

Representative Pyridinium derivatives
(having m as 0 or 1 and —COR$_1$ at position 3)

| | | | | |
|---|---|---|---|---|
| 1 | Structure (a) | — | phenyl | Br |
| 2 | Structure (b) | — | OEt | Br |
| 3 | Structure (c) | — | 2,4-dichlorophenyl | Br |
| 4 | NHNH-(2-pyridyl) | — | OEt | Br |
| 5 | NHNHSO$_2$CH$_3$ | — | 2-thienyl | Br |
| 6 | Structure (d) | — | 2-thienyl | Br |
| 7 | NHCH$_2$CH$_2$OCOPh | — | OEt | Br |
| 8 | NHCH$_2$CH$_2$OCOPh | — | 2,4-dichlorophenyl | Br |
| 9 | NHNH-(2-pyridyl) | — | 2-thienyl | Br |
| 10 | NHNH-(2-pyridyl) | — | phenyl | Br |
| 11 | NHNH$_2$ | — | phenyl | Br |
| 12 | NHNHSO$_2$CH$_3$ | — | phenyl | Br |
| 13 | NHNHSO$_2$CH$_3$ | — | OEt | Br |
| 14 | NHNH-SO$_2$phenyl | — | phenyl | Br |
| 15 | NHNH-SO$_2$phenyl | 2-Cl | phenyl | Br |
| 16 | OCH$_2$CH$_2$OCOCH$_3$ | — | phenyl | Br |
| 17 | OCH$_2$CH$_2$OCOPh | — | OEt | Br |
| 21 | —NHNH—SO$_2$Ph | — | OEt | Br |
| 22 | —OCH$_2$CH$_2$OCH$_3$ | — | 2,4-dichlorophenyl | Br |
| 23 | —NHCH$_2$CH$_2$OCOPh | — | NH phenyl | Cl |
| 24 | —NHNHCONHPh | — | 2-thienyl | Br |
| 25 | NHCH$_2$CH$_2$OCOCH$_3$ | — | phenyl | Br |
| 26 | NHNHSO$_2$Ph | — | NH phenyl | Cl |
| 27 | NHNHSO$_2$Ph(4-CH$_3$) | — | NH phenyl | Cl |
| 28 | OCH$_2$CH$_2$OCOPh | — | phenyl | Br |
| 29 | —NHNHCOPh | — | 2-thienyl | Br |
| 30 | NHNHSO$_2$CH$_2$Ph | — | OEt | Br |
| 31 | NHNHSO$_2$CH$_2$Ph | — | phenyl | Br |
| 32 | Structure (e) | — | 2-furyl | Br |
| 33 | Structure-(f) | — | 2-thienyl | Cl |
| 34 | NHNHCOCH$_2$CH$_2$-cyclohexyl | — | 2-thienyl | Br |
| 35 | NHNHCOCH$_2$CH$_2$-cyclohexyl | — | NH-phenyl | Cl |
| 36 | NHCH$_2$CH$_2$OCO-phenyl | — | 2-thienyl | Br |
| 37 | NHCH$_2$CH$_2$OCO-phenyl | — | CH$_2$CO$_2$-ethyl | Cl |
| 38 | —NHCH$_2$CH$_2$OCH$_3$ | — | -2,4-dichlorophenyl | Br |
| 39 | Structure-(g) | — | NH-cyclopropyl | Cl |
| 40 | —NHCH$_2$CH$_2$OCH$_3$ | — | NH-cyclopropyl | Cl |
| 41 | Structure-(h) | — | NH-isopropyl | Cl |
| 42 | Structure-(i) | — | 2-thienyl | Cl |
| 43 | NHNHSO$_2$CH$_3$ | — | NH-isopropyl | Cl |
| 44 | NHNHSO$_2$CH$_3$ | — | 1-pyrrolidinyl | Cl |
| 45 | NHNHSO$_2$CH$_3$ | — | 2-thienyl | Cl |
| 46 | Structure-(j) | — | —OH | Cl |
| 47 | NHCH$_2$CH$_2$OCH$_3$ | 3-bromo | 2-thienyl | Cl |
| 48 | Structure-(k) | — | 2-thienyl | Cl |
| 49 | Structure-(l) | — | 2-thienyl | Cl |
| 50 | —NHNHSO$_2$isopropyl | — | 2-thienyl | Br |
| 51 | —NHNHSO$_2$CH$_3$ | — | Structure (m) | Cl |
| 52 | —NHNHSO$_2$CH$_3$ | — | Structure (n) | Cl |
| 53 | —NHNHSO$_2$CH$_3$ | 3-bromo | 2-thienyl | Br |
| 54 | —NHNHCOC$_2$H$_5$ | — | 2-thienyl | Br |
| 55 | —NHNHSO$_2$CH$_3$ | — | 5-chloro-2-thienyl | Br |
| 56 | Structure (o) | — | 4-nitro-2-thienyl | Cl |
| 57 | —NHNHSO$_2$CH$_3$ | 2-methyl | 2-thienyl | Br |
| 58 | Structure (p) | — | 5-methyl-2-thienyl | Cl |
| 59 | Structure (q) | — | Structure (n) | Cl |
| 60 | Structure (r) | — | 2-thienyl | Cl |
| 61 | —NHNHSO$_2$CH$_3$ | — | Structure (s) | Cl |
| 62 | Structure (t) | — | 5-chloro-2-thienyl | Cl |
| 63 | —NHNHSO$_2$CH$_3$ | — | 5-methyl-2-thienyl | Cl |
| 64 | —NHNHSO$_2$CH$_3$ | — | 4-nitro-2-thienyl | Br |
| 65 | —NHNHPh | — | —NHPh | Cl |
| 67 | —NHNHSO$_2$CH$_3$ | — | 5-nitro-2-thienyl | Cl |
| 68 | —NHNHSO$_2$CF$_3$ | — | 2-thienyl | Br |
| 69 | —NHNHPh | — | 2-thienyl | Br |
| 70 | —NHNHSO$_2$-4-methoxy-Phenyl | — | 2-thienyl | Br |
| 71 | —NHNHCONHPh | — | —OEt | Br |
| 72 | —NHNHSO$_2$-4-methyl-Phenyl | — | —OEt | Br |
| 73 | —NHNHCONHPh | — | Ph | Br |

TABLE 1A-continued
Representative Pyridinium derivatives
(having m as 0 or 1 and —COR$_1$ at position 3)
| 74 | —NHNHSO$_2$CH$_2$Ph | — | —NHPh | Cl |
| 76 | —NHNHPh | — | Ph | Br |
| 78 | —NHNHPh | — | —OEt | Br |
| 79 | —NHNHSO$_2$-4-methoxy-Phenyl | — | Ph | Br |
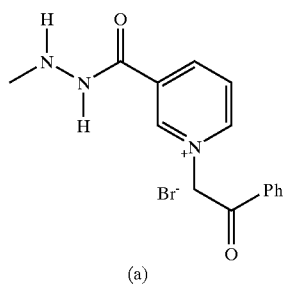
(a)
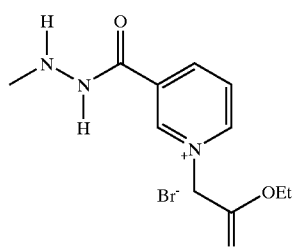
(b)
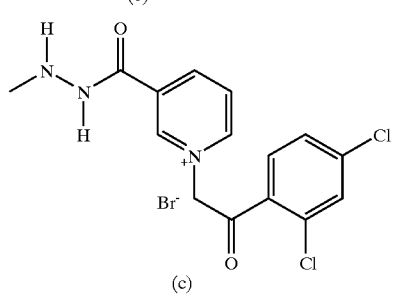
(c)
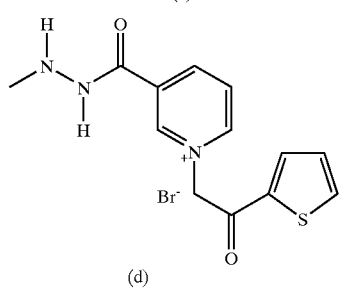
(d)
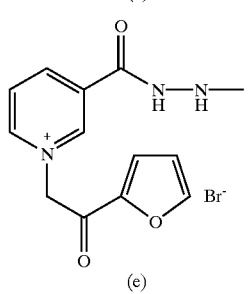
(e)
TABLE 1A-continued
Representative Pyridinium derivatives
(having m as 0 or 1 and —COR$_1$ at position 3)
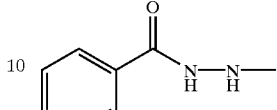
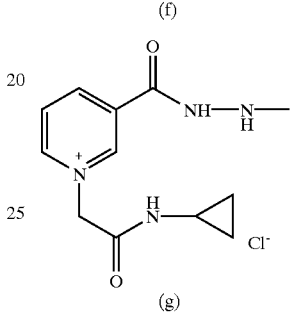
(f)
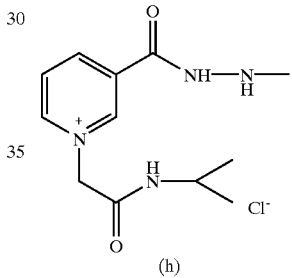
(g)
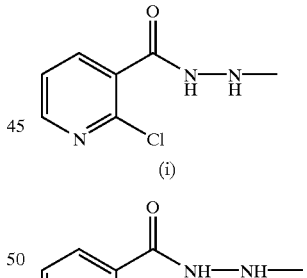
(h)
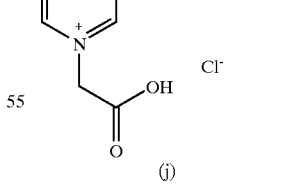
(i)
(j)
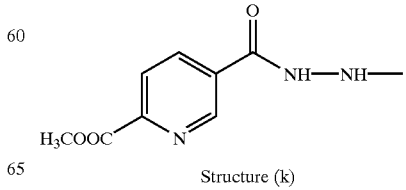
Structure (k)

TABLE 1A-continued

Representative Pyridinium derivatives
(having m as 0 or 1 and —COR₁ at position 3)

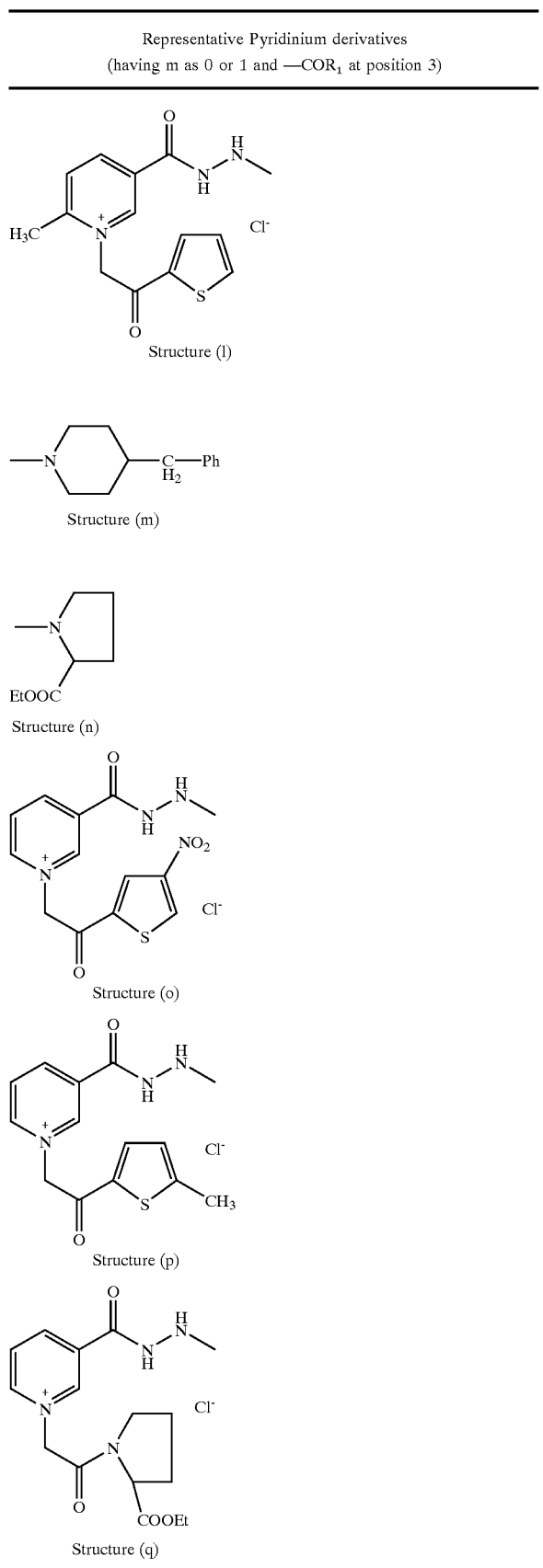

Structure (l)

Structure (m)

Structure (n)

Structure (o)

Structure (p)

Structure (q)

Structure (r)

Structure (S)

Structure (t)

TABLE 1B

Representative Pyridinium derivatives
(having m as 0 and —COR₁ at position 4)

| Compound | —R₁ | —R₂ | —R₃ | —X |
|---|---|---|---|---|
| 18 | NHCH₂CH₂OCOPh | — | 2-thienyl | Br |
| 19 | NHNHSO₂Ph | — | OEt | Br |
| 20 | NHNHSO₂Ph | — | NH phenyl | Cl |
| 66 | —NHCH₂CH₂OCOPh | — | —NHPh | Cl |
| 75 | —NHNHSO₂CH₃ | — | —Ph | Br |
| 77 | —NHCH₂CH₂OCOPh | — | —OEt | Br |
| 80 | —NHCH₂CH₂OCOPh | — | —Ph | Br |
| 81 | —NHNHSO₂CH₃ | — | —OEt | Br |

According to the embodiment of the present invention, the present compounds are used for the treatment of diabetic complications, and aging related vascular and neurovascular complications including kidney disease, nerve damage, atherosclerosis, retinopathy, inflammatory disorders, immunological disorders, oxidative stress, dermatological conditions, and cosmetic conditions including colouration of teeth occurring due to the higher levels of preformed AGE. The increased levels of preformed AGE can be brought under control by breaking the AGE products using compounds mentioned in the invention.

The invention also provides a process for the preparation of novel compounds of the pyridinium series.

The said process for the preparation of compound 1, comprises, adding a solution of phenacyl bromide in isopropanol to N,N'-bis(nicotinyl)hydrazine dissolved in methanol, refluxing for six hours, cooling, filtering the precipitated solid, washing the solid with hot ethyl acetate and finally purifying the solid with 20 ml of methanol ethyl acetate (3:1) to yield the desired compound.

Similarly, the other novel compounds of general formula I, are prepared from properly substituted pyridine derivatives followed by quarternization with appropriate reagent by refluxing in alcoholic solvents like, methanol, ethanol, propanol, etc and high boiling solvents like toluene or xylene etc, for 6–48 hrs. to give the desired compounds.

The examples of substituted pyridine derivatives which can be used for preparation of specific compounds of the invention are given below:

1. N,N'-bis(nicotinyl)hydrazine
2. 3-[(2-pyridyl)hydrazinocarbonyl]pyridine
3. 3-[2-methanesulfonyl)hydrazinocarbonyl]pyridine
4. 3-[(2-benzoyloxy)ethylaminocarbonyl]pyridine
5. 3-[(2-phenylsulfonyl)hydrazinocarbonyl]pyridine
6. 3-[(2-acetoxy)ethyloxycarbonyl]pyridine
7. 3-[(2-benzoyloxy)ethyloxycarbonyl]pyridine
8. 3-[(2-methoxy)ethyloxycarbonyl]pyridine
9. 3-[(2-phenylaminocarbonyl)hydrazinocarbonyl]pyridine
10. 3-[(2-acetoxy)ethylaminocarbonyl]pyridine
11. 3-[(2-(4-methylphenyl sulfonylhydrazinocarbonyl))] pyridine
12. 3-[(2-benzoyl)-hydrazinocarbonyl]pyridine
13. 3-[(2-phenylmethane sulfonyl)hydrazino carbonyl] pyridine
14. 3-[(2-(3-cyclohexylpropanoyl)hydrazino carbonyl] pyridine
15. 3-[(2-methoxy)ethylaminocarbonyl]pyridine
16. 3-[1-oxo-1-(2-methoxycarbonyl)pyridyl]hydrazino pyridine The examples of quaternizing agents which may be used in the reaction are given below:

1. 2-bromoacetyl thiophene
2. 2-chloroacetyl thiopene
3. phenacylbromide
4. phenacylchloride
5. 2,4-dichloropheanacylbromide
6. N-phenyl chloroacetamide
7. N-cyclopropyl chloroacetamide
8. ethylbromoacetate
9. bromo acetylfuran
10. N-isopropylchloroacetamide
11. N-chloroacetyl-2-pyrrolidinone
12. chloroacetic acid In-vitro Screening for AGE-breaking Activity The in vitro AGE formation, studied in the laboratory, by incubating reducing sugar glucose, with protein bovine serum albumin, resulted in browning of solution and increase in the fluorescence. Fluorescence was used as the criteria to monitor the increased AGE formation.

EXAMPLE 1

AGE breaker Activity has been Confirmed by the Screening Procedure as Mentioned Below Materials
   Bovine serum albumin (fraction V) (BSA)
   Glucose, analytical grade
   Phosphate buffered saline (PBS)
Equipment
   Microplate ELISA Reader—Spectramax Plus (Molecular Devices, USA)
   Microplate washer, (Bio-Tec Instruments, USA) pH meter Methods of Experiment Elisa (Enzyme Linked Immunosorbent Assay) 160 mg/ml of protein, bovine serum albumin, BSA and 1.6M glucose sugar were dissolved in phosphate buffered saline, PBS. Sodium azide was added at 0.02% concentration as a preservative. The solution was filtered aseptically through a 0.22 $\mu$M filter and kept for aging at 37° C. for 16 weeks. After 16 weeks the solution was dialyzed against PBS, aliquoted and stored at −20° C.

To determine the AGE breaking activity, 10 $\mu$g/ml of the 16 weeks AGE-BSA was incubated with different concentrations of the test compounds at 37° C. for 24 hours and AGE breaking activity of the test compounds by ELISA was determined.

ELISA was Performed as Follows

1. Different concentrations of 16 weeks AGE-BSA were coated on a microtitre plate as standard. Each concentration is coated in triplicates.
2. The test samples were coated on microtitre plate at a concentration of 5 ng. to 20 ng per well in triplicates.
3. The plate was incubated at 37° C. for one hour.
4. After incubation the plate was washed with PBST (PBS with 0.05% Tween 20).
5. Blocking with 5% skimmed milk in PBS at 37° C. for one hour was done.
6. The plate was washed with PBST.
7. Primary antibody against AGE-BSA was added and the plate is incubated at 37° C. for one hour.
8. The plate was washed with PBST
9. Secondary antibody anti rabbit HRPO (Horse-Radish Per Oxidase) conjugate was added and the plate is incubated at 37° C. for one hour.
10. The plate was washed with PBST.
11. Colour development with OPD (orthophenylenediamine dihydrochloride) and hydrogen peroxide was done.
12. OD (optical density) at (450 nm reading–620 nm reading) was measured after incubation at 37° C. for 15 minutes with Microplate ELISA Reader.

The breaker activity of the compounds were determined by the following formula:

$$\% \text{ Breaker activity} = \frac{OD_{450-620} Control - OD_{450-620} Test}{OD_{450-620} Control} \times 100$$

OD$_{450-620}$Control=Absorbance of 20 ng AGE-BSA after incubation at 37° C. for 24 hours without test compound OD$_{450-620}$ Test=Absorbance of 20 ng AGE-BSA after incubation at 37° C. for 24 hours with required concentration of test compound Using specific examples, the % AGE breaking activity was calculated and recorded in Table 2.

TABLE 2

| Sample | Concentration | % Breakage |
| --- | --- | --- |
| PTB | 10 mM | 27 |
|  | 20 mM | 47 |
| Compound 1 | 5 mM | 13 |
| Compound 4 | 10 mM | 30 |
| Compound 5 | 10 mM | 16 |
|  | 50 mM | 68 |
| Compound 6 | 5 mM | 53 |
| Compound 7 | 20 mM | 36 |

TABLE 2-continued

| Sample | Concentration | % Breakage |
|---|---|---|
| Compound 16 | 10 mM | 16 |
| Compound 17 | 10 mM | 19 |
| Compound 22 | 10 mM | 13 |
|  | 25 mM | 41 |
| Compound 23 | 10 mM | 37 |
|  | 25 mM | 90 |
| Compound 32 | 10 mM | 14 |
| Compound 33 | 5 mM | 20 |
| Compound 38 | 5 mM | 17.66 |
| Compound 39 | 5 mM | 22.8 |
| Compound 40 | 10 mM | 12.38 |
| Compound 42 | 10 mM | 12.51 |
| Compound 43 | 10 mM | 10.85 |
| Compound 45 | 10 mM | 17.53 |
| Compound 47 | 10 mM | 32.38 |
| Compound 49 | 2.5 mM | 85.67 |
| Compound 50 | 10 mM | 31.45 |
| Compound 51 | 10 mM | 20.94 |
| Compound 52 | 10 mM | 25.34 |
| Compound 53 | 2.5 mM | 29.36 |
| Compound 54 | 10 mM | 33.43 |
| Compound 55 | 10 mM | 40.85 |
| Compound 56 | 10 mM | 75.92 |
| Compound 57 | 1.0 mM | 77.69 |
| Compound 58 | 10 mM | 81.95 |
| Compound 59 | 10 mM | 20.31 |
| Compound 60 | 1 mM | 95.36 |
| Compound 61 | 10 mM | 25.06 |
| Compound 62 | 10 mM | 78.41 |
| Compound 63 | 10 mM | 25.17 |
| Compound 64 | 10 mM | 60.94 |
| Compound 65 | 2.5 mM | 68.35 |
| Compound 66 | 10 mM | 19.07 |
| Compound 67 | 1 mM | 42.01 |
| Compound 68 | 10 mM | 92.64 |

Hence compounds 4, 6, 23, 33, 39, 47, 49, 50, 53–58, 60, 62, 64, 65, 67 and 68 have superior AGE breaking activity compared to PTB, of which the potency of compounds 49, 56–58, 60, 62, 64, 65, 67 and 68 are significantly much higher.

In-vivo Screening for AGE-breaking Activity

The test compounds were studied for their beneficial effects on diabetic neuropathy and nephropathy in a rat model of diabetes. The rats were divided into three groups. The first group consisted of age matched untreated non-diabetic animals. The second group consisted of diabetic controls and the third group was the diabetic group treated with the test compound. Each treatment group had its own corresponding control and diabetic groups. The second and third groups were treated with Streptozotocin (STZ) at 60 mg/kg for the induction of diabetes. After completion of 12 weeks of diabetes the rats were treated with the test compound daily (doses shown in table) for a period of 8 weeks. At the end of the treatment the creatinine clearances and nerve conduction velocities (NCV) of the animals were estimated.

Creatinine clearances of the rats were estimated as follows

Creatinine clearance =

$$\frac{\text{Concentration of creatinine in the urine}}{\text{Concentration of creatinine in the blood}} \times \text{ml urine passed/minute}$$

The creatinine clearance in untreated diabetic group was compared with the treated group and the percentage improvements are shown in the Table 3.

The nerve conduction velocity was measured using a modified method of Biro et al 1998. Briefly under ether anesthesia the sciatic and tibial nerves were electrically stimulated at the sciatic notch or ankle, respectively. Electromyograms (EMG's) recorded from the plantar muscles consisted of two components: (1) the short latency direct motor response (M) and the monosynaptically elicited long-latency sensory response (H, Hoffmann reflex). Latency and the duration of the M responses were measured and the motor nerve conduction velocity (MNCV) was calculated as follows:

$$MNCV = \frac{\text{Distance between the sciatic and tibial stimulation points}}{\text{Differences of the latency for } M_{sciatic} \text{ and } M_{tibial}}.$$

The percentage improvement in the nerve conduction velocities in the group treated with the test compounds was calculated as follows:

% Improvement in the $NCV's$ =

$$\frac{NCV \text{ of the treated group} - NCV \text{ of the diabetic group}}{NCV \text{ of the control group} - NCV \text{ of the diabetic group}}.$$

TABLE 3

Effect of compound Nos 33 and 39 on the creatinine clearance and nerve conduction velocities:

| Parameters | Compound No. 33 (7.5 mg/kg, b.i.d.) | Compound No. 39 (6.0 mg/kg, b.i.d.) |
|---|---|---|
| % Increase in creatinine clearance | 103.0 | 5.0 |
| % Increase in the NCV | 60.0 | 58.4 |

The results show that compounds of this class have beneficial effects on creatinine clearance and nerve conduction velocities.

Discussion of the Test Results

All the test compounds mentioned in the current application have shown an invitro AGE-breaker effect. Under conditions of chronic hyperglycemia in rats there is a spontaneous non-enzymatic reaction between glucose, lipids and proteins that leads to the formation of advanced glycosylation end products. In this animal model decreased creatinine clearance and decreased nerve conduction velocity have been demonstrated. These changes are related to damage to renal and neuronal tissues. During chronic NIDDM patients, there is a decrease in the creatinine clearances as a manifestation of the diabetes induced renal damage. One of the major factors contributing to renal damage is the glycation of the long-lived proteins in the kidney. It is well recognized that there is a decrease in the nerve conduction velocities in chronic diabetic subjects, which is a manifestation of neuropathy. Breaking of cross-linked proteins in the neuronal tissues and associated vasculature could lead to an improvement in the neuronal function.

The compounds of the present invention have shown a functional improvement both in terms of the improvement in the creatinine clearance and an improvement in the nerve conduction velocities. The evidences stated above clearly demonstrate that these compounds could play a major role in the prevention and treatment of various diabetic and aging related complications like nephropathy and neuropathy.

The following examples give method of preparation of the specific novel compounds of the invention as given in Table 1. The following compounds suggested are by way of example alone and in no way restrict the invention.

EXAMPLE 2

Pyridinium, 3,3'-(hydrazodicarbonyl)bis[1-(2-oxo-2-phenylethyl)dibromide (Compound 1)

To a boiling solution of N,N'-bis-(nicotinyl)hydrazine (1.21 g., 0.005 mol.) in methanol (20 ml.), a solution of phenacyl bromide (1.99 g., 0.01 mol.) in isopropanol (10 ml.) was added and the reaction mixture was refluxed for 6 hrs. The reaction mixture was concentrated under vacuum (~10 ml.) and filtered. The obtained residue was washed with hot ethylacetate and then the isolated solid was powdered. It was recrystallised from a mixture of methanol and ethylacetate (3:1, 20 ml) to afford a pale yellow solid.

Yield: 60% m.p.: 260–262° C. (decomp.)

IR(KBr, $cm^{-1}$): 1696 and 1680

$^1$H NMR (DMSOd$_6$, 400 MHz) δ: 11.65(2H,s), 9.56(2H, s), 9.21–9.16(4H,m), 8.49–8.45 (2H,m), 8.08–8.05 (4H,d), 7.81–7.77(2H,m), 7.68–7.64 (4H,m), 6.58 (4H,s)

Mass (m/z): 479, 480

According to the above mentioned procedure the following compounds are synthesized by reacting the corresponding pyridine derivatives with appropriate reagents by refluxing in methanol, ethanol, propanol, toluene or xylene for 6–48 hrs. to get the desired compounds:

EXAMPLE 3

Pyridinium, 3,3'-(hydrazodicarbonyl)bis[1-(2-ethoxy-2-oxoethyl)-, dibromide (Compound 2)

Yield: 47% m.p.: 180–182° C. (decomp.)

IR(KBr, $cm^{-1}$): 1744, 1664

$^1$H NMR (DMSOd$_6$, 400 MHz) δ: 11.65 (2H,s), 9.62 (2H,s), 9.28–9.26 (2H,d), 9.17–9.15 (2H,d), 8.47–8.44 (2H,m), 5.77 (4H,s), 4.26 (4H,q), 1.27 (6H,t)

Mass (m/z): 415, 416

EXAMPLE 4

Pyridinium, 3,3'-(hydrazodicarbonyl)bis[1-[2-(2,4-dichlorophenyl)-2-oxoethyl]-, dibromide (Compound 3)

Yield: 24% m.p.: 225–227° C. (decomp.)

IR (KBr, cm$^-$): 1702, 1666

$^1$H NMR (DMSOd$_6$, 400 MHz) δ: 11.69 (2H,s), 9.58 (2H,bs), 9.20–9.18 (4H,m), 8.49–8.47 (2H,m), 8.17–8.15 (2H,d), 7.92 (2H,bs), 7.78–7.76 (2H,d), 6.50 (4H,s)

Mass (m/z): 615, 617, 618, 620.

EXAMPLE 5

Pyridinium, 1-(2-ethoxy-2-oxoethyl)-3-[[2-(2-pyridinyl)hydrazino]carbonyl]-, bromide (Compound 4)

Yield: 16% m.p.: 210–212° C.

IR (KBr, $cm^{-1}$): 3140, 3005, 1732 and 1690

$^1$H NMR (DMSOd$_6$, 400 MHz) δ: 9.63 (1H,s), 9.27 (2H,d), 8.49–8.45 (1H,m) 8.13–8.07 (2H,m), 7.32–7.30 (1H,m), 7.12–7.11(1H,m), 5.77 (2H,s), 4.23 (2H,q), 1.25 (3H,t)

Mass (m/z): 301, 302

EXAMPLE 6

Pyridinium, 3-[[2-(methylsulfonyl)hydrazino]carbonyl]-1-[2-oxo-2-(2-thienyl)ethyl]-, bromide (Compound 5)

Yield: 30% m.p.: 199–200° C.

IR (KBr, $cm^{-1}$): 1714, 1673

$^1$HNMR (DMSOd$_6$, 400 MHz) δ: 11.38 (1H,s), 9.97 (1H,s) 9.51 (1H,s), 9.16 (1H,d), 9.06–9.04 (1H,m), 8.43–8.39 (1H,m), 8.25–8.21 (2H,m), 7.43–7.41 (1H,t), 6.45 (2H,s), 3.08 (3H,s).

Mass (m/z): 340, 341, 342

EXAMPLE 7

Pyridinium, 3,3'-(hydrazodicarbonyl)bis[1-[2-oxo-2-(2-thienyl)ethyl]-, dibromide (Compound 6)

Yield: 33% m.p.: 259–261° C. (decomp.)

IR (KBr, $cm^{-1}$): 3330, 1702, 1674, 1655 and 1626

$^1$H NMR (DMSOd$_6$, 400 MHz) δ: 11.59 (2H,s), 9.50 (2H,s), 9.15–9.08 (4H,m), 8.40–8.36 (2H,m), 8.17–8.14 (4H,m), 7.33(2H,t), 6.42 (4H,s)

Mass (m/z): 491, 492.

EXAMPLE 8

Pyridinium, 3-[[[2-(benzoyloxy)ethyl]amino]carbonyl]-1-(2-ethoxy-2-oxoethyl)-, bromide (Compound 7)

Yield: 85% m.p.: 132–134° C.

IR (KBr, $cm^{-1}$): 3210, 3067, 1726, 1687, 1656

$^1$H NMR (DMSOd$_6$, 400 MHz) δ: 9.46 (1H,s), 9.37 (1H,t), 9.11(1H,t), 8.97 (1H,d), 8.33–8.29 (1H,m) 7.95–7.93 (2H,m), 7.63–7.59 (1H,m), 7.49–7.45 (2H,m), 5.65 (2H,s), 4.39 (2H,t), 4.19 (2H,q), 3.70–3.69 (2H,m), 1.20 (3H,t)

Mass (m/z): 357, 358, 359

EXAMPLE 9

Pyridinium, 3-[[[2-(benzoyloxy)ethyl]amino]carbonyl]-1-[2-(2,4-dichlorophenyl)-2-oxoethyl]-, bromide (Compound 8):

Yield: 75% m.p.: 102–104° C.

IR(KBr, $cm^{-1}$): 1703, 1685, 1675

$^1$H NMR (DMSOd$_6$, 400 MHz) δ: 9.41–9.37 (2H,m), 9.03–8.98 (2H,m)8.34–8.30 (1H,m), 8.04 (1H,d), 7.91–7.89 (2H,m), 7.82 (1H,d), 7.68–7.65 (1H,m), 7.58–7.55 (1H,m), 7.43 (2H,t), 6.35 (2H,s), 4.36 (2H,t), 3.68–3.64 (2H,m)

Mass (m/z): 457, 458, 459, 460, 461, 462

EXAMPLE 10

Pyridinium, 1-[2-oxo-2-(2-thienyl)ethyl]-3-[[2-(2-pyridinyl)hydrazino]carbonyl]-, bromide (Compound 9)

Yield: 10% m.p.: 212–214° C. (decomp)

IR(KBr, cm$^{-1}$): 1685, 1649

$^1$H NMR (DMSOd$_6$, 400 MHz) δ: 11.21 (1H,bs), 9.59 (1H,s), 9.19 (2H,d), 8.44 (1H,t), 8.27–8.24 (2H,m), 8.08 (1H,bs), 7.62 (1H,bs), 7.44 (1H,t), 6.85–6.79 (2H,m), 6.50 (2H,s)

Mass (m/z): 339, 340, 341

EXAMPLE 11

Pyridinium, 1-(2-oxo-2-phenylethyl)-3-[[2-(2-pyridinyl)hydrazino]carbonyl]-, bromide (Compound 10)

Yield: 4% m.p.: 190° C. (decomp)

IR(KBr, cm$^{-1}$): 1683, 1670, 1648

$^1$H NMR (DMSOd$_6$, 400 MHz) δ: 11.14 (1H,bs), 9.53 (1H,s), 9.18–9.13 (2H,m), 8.45–8.42 (1H,t), 8.08–8.06 (3H,m), 7.80 (1H,t), 7.67 (2H,t), 7.62–7.55 (1H,m), 6.83–6.76 (2H,m), 6.54 (2H,s)

Mass (m/z): 333, 334, 335

EXAMPLE 12

Pyridinium, 3-(hydrazinocarbonyl)-1-(2-oxo-2-phenylethyl)-, bromide (Compound 11)

Yield: 15% m.p.: 215–216° C.

IR(KBr, cm$^{-1}$): 1695, 1680

$^1$HNMR (DMSOd$_6$, 400 MHz) δ: 10.25 (1H,s) 9.65 (1H,s), 9.35–9.32 (2H,m), 8.90–8.88 (1H,m) 8.50–8.46 (2H,d), 8.21–8.17 (1H,m), 8.05–8.07 (2H,m), 6.50 (2H,s), 4.45 (2H,s).

Mass (m/z): 256, 257.

EXAMPLE 13

Pyridinium, 3-[[2-(methylsulfonyl)hydrazino]carbonyl]-1-(2-oxo-2-phenylethyl)-, bromide (Compound 12)

Yield: 35% m.p.: 227–228° C.

IR(KBr, cm$^{-1}$): 1710, 1702

$^1$HNMR (DMSOd$_6$, 400 MHz) δ: 11.30, (1H,s), 9.88 (1H,s), 9.41 (1H,s), 9.06–9.05 (1H,d) 8.98–8.96 (1H,d), 8.34–8.31 (1H,m), 7.97 (2H,d), 7.72–7.69 (1H,t), 7.59–7.56 (2H,t), 6.44 (2H,s), 2.99 (3H,s)

Mass (m/z): 334, 335

EXAMPLE 14

Pyridinium, 1-(2-ethoxy-2-oxoethyl)-3-[[2-(methylsulfonyl)hydrazino]carbonyl]-, bromide (Compound 13)

Yield: 38% m.p.: 75–76° C.

IR(KBr, cm$^{-1}$): 1739, 1697

$^1$HNMR (DMSOd$_6$, 400 MHz) δ: 11.39 (1H,s), 9.96 (1H,s), 9.56 (1H,s), 9.23 (1H,d), 9.06 (1H,d), 8.40 (1H,t), 5.75 (2H,s), 4.27–4.22 (2H,q), 3.08 (3H,s), 1.26 (3H,t)

Mass (m/z): 301, 302, 303

EXAMPLE 15

Pyridinium, 1-(2-oxo-2-phenylethyl)-3-[[2-(phenylsulfonyl)hydrazino]carbonyl]-, bromide (Compound 14)

Yield: 28% m.p.: 187–188° C.(dec.)

IR(KBr, cm$^{-1}$): 1700, 1633

$^1$HNMR (DMSOd$_6$, 400 MHz) δ: 11.38 (1H,s), 10.45 (1H,s), 9.33(1 H,s), 9.13–9.12 (1H,d), 8.95 (1H,d), 8.38 (1H,t), 8.05 (2H,d), 7.89 (2H,d), 7.80 (1H,t), 7.66 (3H,t), 7.57 (2H,t), 6.50 (2H,s).

Mass (mn/z): 396, 397, 398

EXAMPLE 16

Pyridinium, 2-chloro-1-(2-oxo-2-phenylethyl)-3-[[2-(phenylsulfonyl)hydrazino]carbonyl]-, bromide (Compound 15)

Yield: 23% m.p.: 247–250° C. (decomp)

IR(KBr, cm$^{-1}$): 1685, 1679, $^1$HNMR (DMSOd$_6$, 400 MHz) δ: 11.12 (1H,s), 9.49 (1H,s), 9.07–9.03(1H,m), 8.44 (1H, t), 8.07 (2H,d), 7.80 (1H,t), 7.67 (2H,t), 7.18 (2H,t), 6.87 (2H,d), 6.77 (1H,t), 6.50 (2H,s).

Mass (m/z): 430, 431, 432

EXAMPLE 17

Pyridinium, 3-[[2-(acetyloxy)ethoxy]carbonyl]-1-(2-oxo-2-phenylethyl)-, bromide (Compound 16)

Yield: 40% m.p.: 152–153° C.

IR(KBr, cm$^{-1}$): 1737, 1691, 1635

$^1$HNMR (DMSOd$_6$, 400 MHz) δ: 9.63 (1H,s), 9.24 (1H,d), 9.12 (1H,d), 8.43 (1H,t), 8.07 (2H,d), 7.80 (1H,t), 7.67 (2H,t), 6.59 (2H,s), 4.62–4.60 (2H,m), 4.39–4.37 (2H,m), 2.03 (3H,s)

Mass (m/z): 328, 329

EXAMPLE 18

Pyridinium, 3-[[2-(benzoyloxy)ethoxy]carbonyl]-1-(2-ethoxy-2-oxoethyl)-, bromide (Compound 17)

Yield: 35% m.p.: 142–143° C.

IR(KBr, cm$^{-1}$): 1736, 1718, 1636

$^1$HNMR (DMSOd$_6$, 400 MHz) δ: 9.60 (1H,s), 9.20–9.18 (1H,d), 9.04–9.02 (1H,d), 8.33–8.29 (1H,m), 7.90–7.88 (2H,d), 7.58–7.57 (1H,m), 7.46–7.42 (2H,m), 5.67 (2H,s), 4.71–4.68 (2H,m), 4.58–4.56 (2H,m), 4.15 (2H,q), 1.16 (3H,t)

Mass (m/z): 358, 359, 360

EXAMPLE 19

Pyridinium, 4-[[[2-(benzoyloxy)ethyl]amino]
carbonyl]-1-[2-oxo-2-(2-thienyl)ethyl]-, bromide
(Compound 18)

m.p.: 210–211° C.

IR(KBr, cm$^{-1}$): 1723, 1680, 1668

$^1$HNMR (DMSOd$_6$, 400 MHz) δ: 9.52 (1H,t), 9.14 (2H,d), 8.50 (2H,d), 8.25–8.21 (2H,m), 8.01–7.99 (2H,d), 7.67 (1H,t), 7.55–7.51 (2H,m), 7.42–7.40 (1H,m), 6.42 (1H,s) 4.47–4.45 (2H,t), 3.77–3.73 (2H, m).

Mass (m/z): 395, 396

EXAMPLE 20

Pyridinium, 1-(2-ethoxy-2-oxoethyl)-4-[[2-
(phenylsulfonyl)hydrazino]carbonyl]-, bromide
(Compound 19)

Yield: 60% m.p.: 171–173° C.

IR (KBr, cm$^{-1}$): 1745, 1685, 1645.

$^1$HNMR (DMSOd$_6$, 400 MHz) δ: 11.41 (1H,s), 10.39 (1H,s), 9.10 (2H,d), 8.27 (2H,d), 7.82–7.80 (2H,d), 7.60–7.57 (1H,t), 7.50–7.46 (2H,t), 5.63 (2H,s), 4.18–4.12 (2H,q), 1.19–1.15 (3H,t).

Mass (m/z): 364, 365, 366

EXAMPLE 21

Pyridinium, 1-[2-oxo-2-(phenylamino)ethyl]-4-[[2-
(phenylsulfonyl)hydrazino]carbonyl]-, bromide
(Compound 20)

Yield: 10% m.p.: 225–227° C.

IR (KBr, cm$^{-1}$): 1693, 1642, 1592

$^1$HNMR(DMSOd$_6$, 400 MHz) δ: 11.55 (1H,s), 10.99 (1H,s), 10.49 (1H,s), 9.20 (2H,d), 8.34 (2H,d), 7.89 (2H,d), 7.73–7.64 (1H,t), 7.61–7.56 (4H,m), 7.37–7.33 (2H,t), 7.12–7.09 (1H,t), 5.73 (2H,s).

Mass (m/z): 411, 412, 413, 414

EXAMPLE 22

Pyridinium, 1-(2-ethoxy-2-oxoethyl)-3-[[2-
(phenylsulfonyl)hydrazino]carbonyl]-, bromide
(Compound 21)

Yield: 75% m.p.: 145–147° C.

IR(KBr cm$^{-1}$): 1744, 1713, 1633

$^1$HNMR (DMSOd$_6$, 400 MHz) δ: 11.27(1H,s), 10.36 (1H,s), 9.28 (1H,s), 9.09 (1H,d), 8.83 (1H,d), 8.27–8.24 (1H,m), 7.82–7.79 (2H,m), 7.58 (1H,t), 7.48 (2H,t), 5.59 (2H,s), 4.17–4.12 (2H, q), 1.16 (3H,t).

Mass (m/z): 364, 365, 366

EXAMPLE 23

Pyridinium, 1-[2-(2,4-dichlorophenyl)-2-oxoethyl]-
3-[(2-methoxyethoxy)carbonyl]-, bromide
(Compound 22)

Yield: 25% m.p.: 156–158° C.

IR (KBr, cm$^{-1}$): 1731, 1706, 1640

$^1$HNMR (DMSO d$_6$, 400 MHz) δ:9.61 (1H,s), 9.20 (1H,d), 9.13 (1H,d), 8.45–8.41 (1H,m), 8.15 (1H,d), 7.92 (1H,d), 7.78–7.76 (1H,m), 6.49 (2H,s), 4.56–4.54 (2H,m), 3.72–3.69 (2H,q), 3.31 (3H,s).

Mass (m/z): 368, 369, 370, 371

EXAMPLE 24

Pyridinium, 3-[[[2-(benzoyloxy)ethyl]amino]
carbonyl]-1-[2-oxo-2-(phenylamino)ethyl]-, chloride
(Compound 23)

Yield: 70% m.p.: 171–172° C.

IR (KBr, cm$^{-1}$): 1720, 1692, 1668

$^1$HNMR:(DMSOd$_6$, 400 MHz) δ: 11.06 (1H,s), 9.67 (1H,t), 9.59 (1H,s), 9.20 (1H,d), 9.11 (1H,d), 8.36–8.32(1H, m), 8.00 (2H,d), 7.66–7.61 (3H,m),7.51 (2H,t),7.34 (2H,t), 7.10 (1H,t), 5.77 (2H,s), 4.45 (2H,t), 3.76–3.72 (2H,q).

Mass (m/z): 404, 405, 406, 407

EXAMPLE 25

Pyridinium, 1-[2-oxo-2-(2-thienyl)ethyl]-3-[[2-
[(phenylamino)carbonyl]hydrazino]carbonyl]-,
bromide (Compound 24)

Yield: 30% m.p.: 202–204° C.

IR (KBr, cm$^{-1}$): 1718, 1673

$^1$HNMR : (DMSOd$_6$, 400 MHz) δ: 11.03 (1H,s), 9.55 (1H,s), 9.18 (1H,d), 9.10 (1H,d), 9.00 (1H,s),8.57 (1H,s), 8.46–8.42 (1H,t), 8.25–8.22 (2H,m), 7.47–7.45 (2H,d), 7.43–7.41 (1H,t), 7.29–7.25 (2H,t), 7.0–6.96 (1H,t), 6.46 (2H,s).

Mass (m/z): 381, 382, 383

EXAMPLE 26

Pyridinium, 3-[[[2-(acetyloxy)ethyl]amino]carbonyl-
1-(2-oxo-2-phenylethyl)-, bromide (Compound 25)

Yield: 55% m.p.: 186–188° C.

IR (KBr, cm$^{-1}$): 1734, 1697, 1679

$^1$HNMR (DMSOd$_6$, 400 MHz) δ: 9.47(1H,s), 9.36 (1H,t), 9.13–9.05 (2H,m), 8.42–8.38 (1H,m), 8.06 (2H,d), 7.80 (1H,t), 7.67 (2H,t), 6.54 (2H,s), 4.18 (2H,t), 3.61–3.57 (2H,q), 2.02 (3H,s).

Mass (m/z): 327, 328, 329.

EXAMPLE 27

Pyridinium, 1-[2-oxo-2-(phenylamino)ethyl]-3-[[2-(phenylsulfonyl)hydrazino]carbonyl]-, chloride (Compound 26)

Yield: 38% m.p.: 232–234° C.

IR (KBr, cm$^{-1}$): 1689, 1636, 1596

$^1$HNMR (DMSOd$_6$, 400 MHz) δ: 11.30 (1H,s), 10.80 (1H,s), 10.37 (1H,s), 9.29 (1H,s), 9.09 (1H,d), 8.81 (1H,d), 8.25–8.21 (1H,t), 7.82–7.80 (2H,d), 7.59–7.46 (5H,m), 7.28–7.24 (2H,t), 7.04–7.00 (1H,t), 5.62 (2H,s).

Mass (m/z): 411, 412, 413, 414

EXAMPLE 28

Pyridinium, 3-[[2-[(4-methylphenyl)sulfonyl]hydrazino]carbonyl]-1-[2-oxo-2-(phenylamino)ethyl]-, chloride (Compound 27)

Yield: 48% m.p.: 205–206° C.

IR(KBr, cm$^{-1}$): 1712, 1681, 1632

$^1$HNMR (DMSOd$_6$, 400 MHz) δ: 11.35 (1H,s), 10.86 (1H,s), 10.36 (1H,s), 9.38 (1H,s), 9.17 (1H,d), 8.90 (1H,d), 8.34–8.30 (1H,m), 7.78 (2H,d), 7.59 (2H,d), 7.37–7.33 (4H,m), 7.11 (1H,t), 5.70 (2H,s), 2.36 (3H,s).

Mass (m/z): 425, 426, 427, 428

EXAMPLE 29

Pyridinium, 3-[[2-(benzoyloxy)ethoxy]carbonyl]-1-(2-oxo-2-phenylethyl)-, bromide (Compound 28)

Yield: 35% m.p.: 132–134° C.

IR (KBr, cm$^{-1}$): 1730, 1705, 1690

$^1$HNMR (DMSOd$_6$, 400 MHz) δ: 9.80 (1H,s), 9.36 (1H,d), 9.30 (1H,d), 8.58 (1H,t), 8.21 (2H,d), 8.12 (2H,d), 7.95 (1H,t), 7.85–7.80 (3 H,m), 7.68 (2H,t), 6.71 (2H,s), 4.95–4.93 (2H,m), 4.82–4.80 (2H,m).

Mass (m/z): 390, 391, 392.

EXAMPLE 30

Pyridinium, 3-[(2-benzoylhydrazino)carbonyl]-1-[2-oxo-2-(2-thienyl)ethyl]-, bromide (Compound 29)

Yield: 45% m.p.: 80–81° C.

IR(KBr Cm$^{-1}$): 1700, 1663, 1631

$^1$HNMR (DMSOd$_6$, 400 MHz) δ: 11.49 (1H,s), 10.95 (1H,s), 9.67 (1H,s), 9.34 (1H,d), 9.27 (1H,d), 8.52–8.48 (1H,m), 8.29–8.28 (2H,m), 8.00 (2H,d), 7.68 (1H,t), 7.59 (2H,t), 7.46 (1H,t), 6.63 (2H,s)

Mass (m/z): 366, 367, 368, 369

EXAMPLE 31

Pyridinium, 1-(2-ethoxy-2-oxoethyl)-3-[[2-[(phenylmethyl)sulfonyl]hydrazino]carbonyl]-, bromide (Compound 30)

Yield: 50% m.p.: 147–148° C.

IR (KBr, cm$^{-1}$): 1749, 1698, 1640

$^1$HNMR (DMSOd$_6$, 400 MHz) δ: 11.57 (1H,s), 10.21 (1H,s), 9.75 (1H,s), 9.38 (1H,d), 9.24 (1H,d), 8.59–8.56(1H,m), 7.67–7.65 (2H,m), 7.58–7.52 (3H,m), 5.90 (2H,s), 4.68 (2H,s), 4.45–4.39(2H,q),1.43 (3H,t).

Mass (m/z): 377, 378, 379

EXAMPLE 32

Pyridinium, 1-(2-oxo-2-phenylethyl)-3-[[2-[(phenylmethyl)sulfonyl]hydrazino]carbonyl-, bromide (Compound 31)

Yield: 80% m.p.: 205–207° C.

IR (KBr, Cm$^{-1}$): 1687, 1637

$^1$HNMR (DMSOd$_6$, 400 MHz) δ: 11.59 (1H,s), 10.20 (1H,s), 9.71 (1H,s), 9.33 (1H,d), 9.27 (1H,d), 8.62–8.59 (1H,m), 8.25–8.23 (2H,d), 7.99–7.95 (1H,t), 7.86–7.82 (2H,t), 7.67–7.65 (2H,m), 7.57–7.52 (3H,m), 6.72 (2H,s), 4.69 (2H,s).

Mass (m/z): 410, 411, 412, 413

EXAMPLE 33

Pyridinium, 3,3'-(hydrazodicarbonyl)bis[1-[2-(2-furanyl)-2-oxoethyl]-, dibromide (Compound No: 32)

Yield: 23% m.p.: 267–269° C. (dec)

IR (KBr, cm$^{-1}$): 1687, 1660

$^1$H NMR (DMSO d$_6$, 400 MHz) δ: 11.65 (2H,s), 9.56 (2H,s), 9.21–9.15 (4H,m), 8.48–8.44 (2H,t), 8.23 (2H,s), 7.74–7.73 (2H,d), 6.91–6.90 (2H,d) 6.34 (4H,s)

Mass (m/z): 459, 460, 461

EXAMPLE 34

Pyridinium, 3,3'-(hydrazodicarbonyl)bis[1-[2-(2-thienyl)-2-oxoethyl]-, dichloride (Compound No: 33)

Yield: 35% m.p.: 275–277° C.

IR (KBr, cm$^{-1}$): 3374, 1665,1632, 1410

$^1$H NMR (DMSO d$_6$, 400 MHz) δ: 11.88 (2H,s), 9.66 (2H,s), 9.29–9.24 (4H,m), 8.48–8.44 (2H,m), 8.25–8.23 (4H,m), 7.43–7.41 (2H,m), 6.53 (4H,s).

Mass (m/z): 491, 492, 493, 494

EXAMPLE 35

Pyridinium, 3-[[2-(3-cyclohexyl-1-oxopropyl) hydrazino]carbonyl]-1-[2-oxo-2-(2-thienyl)ethyl]-, bromide (Compound No: 34)

Yield: 15% m.p.: 217–219° C. (dec)

IR (KBr, cm$^{-1}$): 3190, 1708, 1667 and 1404

$^1$H NMR (DMSO d$_6$, 400 MHz) δ: 11.07 (1H,s), 10.22 (1H,s), 9.51 (1H,s), 9.16–9.15 (1H,d), 9.06–9.04 (1H,d), 8.42–8.40 (1H,m), 8.25–8.21 (2H,m), 7.43–7.40 (1H,m), 6.44 (2H,s), 2.25–2.22 (2H,t), 1.72–1.60 (5H,m), 1.49–1.43 (2H,q), 1.24–1.10 (4H,m), 0.9–0.85 (2H,m)

Mass (m/z): 400,401,402 and 403

EXAMPLE 36

Pyridinium, 3-[[2-(3-cyclohexyl-1-oxopropyl) hydrazino]carbonyl]-1-[2-oxo-2-(phenylamino) ethyl]-, chloride (Compound No: 35)

Yield: 25% m.p.: 234–236° C. (dec)

IR (KBr, cm$^{-1}$): 1689, 1652 and 1625

$^1$H NMR (DMSO d$_6$, 400 MHz) δ: 11.11 (1H,s), 10.95 (1H,s), 10.23 (1H,s), 9.56 (1H,s), 9.23–9.21 (1H,d), 9.06–9.04 (1H,d), 8.38–8.35 (1H,m), 7.62–7.60 (2H,d), 7.37–7.33 (2H,t), 7.12–7.09 (1H,t), 5.75 (2H,s), 2.25–2.22 (2H,t), 1.72–1.60 (5H,m) 1.49–1.43 (2H,m), 1.25–1.10 (4H,m), 0.91–0.83 (2H,m)

Mass (m/z): 409, 410, 411 and 412

EXAMPLE 37

Pyridinium, 3-[[[2-(benzoyloxy)ethyl]amino] carbonyl]-1-[2-oxo-2-(2-thienyl)ethyl]-, bromide (Compound No:36)

Yield: 40% m.p.: 125–127° C.

IR (KBr, cm$^{-1}$): 1710 and 1675

$^1$H NMR (DMSO d$_6$, 400 MHz) δ: 9.48 (1H,s), 9.43–9.41 (1H,t), 9.12–9.11 (1H,d), 9.05–9.02 (1H,d), 8.40–8.36 (1H,m), 8.25–8.20 (2H,m), 8.00–7.98 (2H,m), 7.68–7.64 (1H,m), 7.54–7.50 (2H,m), 7.42–7.40 (1H,m), 6.43 (2H,s), 4.46–4.43 (2H,t), 3.77–3.73 (2H,q)

Mass (m/z): 395, 396, 397 and 398

EXAMPLE 38

Pyridinium, 3-[[[2-(benzoyloxy)ethyl]amino] carbonyl]-1-(4-ethoxy-2,4-dioxobutyl)-, chloride (Compound No: 37)

Yield: 35% m.p.: 147–149° C.

IR (KBr, cm$^{-1}$): 1743, 1720, 1680 and 1627

$^1$H NMR (DMSO d$_6$, 400 MHz) δ: 9.62–9.59 (1H,t), 9.32–9.29 (1H,s), 9.05–9.03 (1H,d), 8.93–8.90 (1H,d), 8.27–8.24 (1H,m), 7.92–7.89 (2H,d), 7.59–7.55 (1H,m), 7.45–7.41 (2H,m), 5.82 (2H,s), 4.37–4.34 (2H,t), 4.08–4.03 (2H,q), 3.80 (2H,s), 3.67–3.63 (2H,q), 1.15–1.11 (3H,t),

Mass (m/z): 399, 400 and 401

EXAMPLE 39

Pyridinium, 3-[[[(2-methoxyethyl)amino]carbonyl]-1-[2-(2,4-dichlorophenyl)-2-oxoethyl]-, bromide (Compound No: 38)

Yield: 70% m.p.: 93–95° C.

IR (KBr, cm$^{-1}$): 1704, 1664 and 1636

$^1$H NMR (DMSO d$_6$, 400 MHz) δ: 9.48 (1H,s), 9.29 (1H,bs), 9.11–9.08 (2H,m), 8.41–8.38 (1H,m), 8.15–8.13 (1H,d), 7.92–7.91 (1H,t), 7.78–7.75 (1H,m), 6.44 (2H,s) 3.52 (2H,bs), 3.51 (2H,bs), 3.28 (3H,s)

Mass (m/z): 367,368,369 and 370

EXAMPLE 40

Pyridinium, 3,3'-(hydrazodicarbonyl)bis[1-[2-(cyclopropylamino)-2-oxoethyl]-, dichloride (Compound No: 39)

Yield: 40% m.p.: 228–230° C.

IR (KBr cm$^{-1}$): 1675, 1636 and 1298

$^1$H NMR (DMSO d$_6$, 400 MHz) δ: 11.85 (2H,s), 9.59 (2H,s), 9.25–9.19 (4H,m), 9.00–8.99 (2H,d), 8.39–8.36 (2H,m), 5.53 (4H,s), 2.73–2.66 (2H,m), 0.78–0.62 (4H,m), 0.53–0.49 (4H,m)

Mass (m/z): 437, 438 and 439

EXAMPLE 41

Pyridinium, 1-[2-(cyclopropylamino)-2-oxoethyl]-3-[[(2-methoxyethyl)amino]carbonyl]-, chloride (Compound No: 40)

Yield: 10% m.p.: 122–124° C.

IR (KBr, cm$^{-1}$): 1661, 1633, 1549 and 1121

$^1$H NMR (DMSO d$_6$, 400 MHz) δ: 9.40 (1H,s), 9.08–9.02 (2H,m), 8.28–8.25 (1H,m), 5.53 (2H,s), 3.66–3.61 (4H,m), 3.39 (3H,s), 2.78–2.74 (1H,m), 0.80–0.75 (2H,m), 0.64–0.61 (2H,m)

Mass (m/z): 278, 279 and 280

EXAMPLE 42

Pyridinium, 3,3'-(hydrazodicarbonyl)bis[1-[2-[(1-methylethyl)amino]-2-oxoethyl]-, dichloride (Compound No: 41)

Yield: 35% m.p.: 114–116° C. (dec)

IR (KBr, cm$^{-1}$): 1707, 1668 and 1637

$^1$H NMR (DMSO d$_6$, 400 MHz) δ: 11.84 (2H,s), 9.59 (2H,s), 9.21–9.18 (4H,m), 8.74–8.72 (2H,d), 8.39–8.35 (2H,m), 5.53 (4H,s), 3.92 3.84 (2H,m), 1.14–1.02 (12H,d)

Mass (m/z): 441, 442 and 443

EXAMPLE 43

Pyridinium, 3-[[2-[(2-chloro-3-pyridinyl)carbonyl] hydrazino]carbonyl]-1-[2-oxo-2-(2-thienyl)ethyl]-, chloride (Compound No: 42)

Yield: 56% m.p.: 233–235° C.

IR (KBr, cm$^{-1}$): 1680, 1637, 1404 and 1293

$^1$H NMR (DMSO d$_6$, 400 MHz) δ: 11.62 (1H,s), 11.05 (1H,s), 9.62 (1H,s), 9.24–9.23 (1H,d), 9.18–9.16 (1H,d), 8.58–8.56 (1H,m), 8.46–8.43 (1H,m), 8.26–8.24 (2H,m), 8.02–8.00 (1H,m), 7.61–7.58 (1H,m), 7.43–7.41 (1H,m), 6.51 (2H,s)

Mass (m/z): 401, 402, 403, 404 and 405

EXAMPLE 44

Pyridinium, 1-[2-[(1-methylethyl)amino]-2-oxoethyl]-3-[[2-(methylsulfonyl)hydrazino]carbonyl]-, chloride (Compound No: 43)

Yield: 10% m.p.: 227–229° C.

IR (KBr, cm$^{-1}$): 1691, 1670, 1566 and 1330

$^1$H NMR (DMSO d$_6$, 400 MHz) δ: 11.55 (1H,s), 9.94 (1H,s), 9.52 (1H,s), 9.16–9.14 (1H,m), 9.09–9.07 (1H,m), 8.72–8.70 (1H,m), 8.34–8.30 (1H,m), 5.50 (2H,s), 3.89–3.84 (1H,m), 3.11 (3H,s), 1.13–1.12 (6H,d)

Mass (m/z): 315, 316 and 317

EXAMPLE 45

Pyridinium, 3-[[2-(methylsulfonyl)hydrazino]carbonyl]-1-[2-oxo-2-(1-pyrrolidinyl)ethyl]-, chloride (Compound No: 44)

Yield: 21.00% m.p.: 205–207° C.

IR (KBr, cm–1): 1699, 1646 and 1589

$^1$HNMR (DMSO d$_6$, 400 MHz) δ: 11.50 (1H,s), 9.94 (1H,s), 9.46 (1H,s), 9.11–9.06 (2H,m), 8.36–8.33 (1H,t), 5.75 (2H,s), 3.55–3.48 (3H,m), 3.10 (3H,s), 2.00–1.95 (2H,m), 1.87–1.81 (2H,m)

Mass (m/z): 327, 328, 329 and 330

EXAMPLE 46

Pyridinium, 3-[[2-(methylsulfonyl)hydrazino]carbonyl]-1-[2-oxo-2-(2-thienyl)ethyl]-, chloride (Compound No: 45)

Yield: 31.00% m.p.: 215–217° C.

IR (KBr, cm$^{-1}$): 1685, 1666 and 1635

$^1$HNMR (DMSO d$_6$, 400 MHz) δ: 11.49, (1H,s), 9.96 (1H,s), 9.55 (1H,s), 9.18 (1 H,d), 9.10 (1H,d), 8.43–8.39 (1H,t), 8.25–8.22 (2H,m), 7.42 (1H,t) 6.47 (2H,s), 3.09 (3H,s).

Mass (m/z): 340, 341, 342 and 343

EXAMPLE 47

Pyridinium, 3,3'-(hydrazodicarbonyl)bis[1-carboxymethyl)-, dichloride (Compound No: 46)

Yield: 43.00% m.p.: 235–240° C. (d)

IR (KBr, cm$^{-1}$): 1743, 1700 and 1672

$^1$HNMR (DMSO d$_6$, 400 MHz) δ: 11.89 (2H,s), 9.69 (2H,s), 9.31–9.29 (2 H,d), 9.25–9.23 (2H,d), 8.43–8.39 (2H,t) 5.70 (4H,s)

Mass (m/z): 360,361,362

EXAMPLE 48

Pyridinium, 3-bromo-5-[[2-methoxyethyl)amino]carbonyl]-1-[2-oxo-2-(2-thienyl)ethyl]-, chloride (Compound No: 47)

Yield: 31.00% m.p.: 180–182° C.

IR (KBr, cm$^{-1}$): 1661 and 1620

$^1$HNMR (DMSO d$_6$, 400 MH$_z$) δ: 9.58–9.54 (2H,d), 9.43–9.39 (2H,d), 8.25–8.21 (2H,m), 7.41 (1H,t), 6.43 (2H,s), 3.51 (4H,m), 3.29 (3H,s).

Mass (m/z): 384, 385, 386, 387 and 388

EXAMPLE 49

Pyridinium, 3-[[2-[[6-(methoxycarbonyl)-3-pyridinyl]carbonyl]hydrazino]carbonyl]-1-[2-oxo-2-(2-thienyl)ethyl]-, chloride (Compound No: 48)

Yield: 30.00% m.p.: 222–225° C.

IR (KBr, cm$^{-1}$): 1726, 1708 and 1662

$^1$H NMR (DMSO d$_6$, 400 MH$_z$) δ: 11.47 (1H,s), 11.23 (1H,s), 9.58 (1H,s), 9.22–9.15 (3H,m), 8.56–8.53 (1H,d), 8.46–8.43 (1H,t),. 8.25–8.21 (3H,m), 7.42 (1H,t), 6.49 (2H,s), 3.95 (3H,s)

Mass (m/z): 425, 426 and 427

EXAMPLE 50

Pyridinium, 2-methyl-1-(2-oxo-2-thien-2-yl-ethyl)-5-[[2-[[-1-(2-oxo-2-thien-2-yl-ethyl)pyridinium-3-yl]carbonyl]hydrazino]carbonyl]-, dichloride (Compound No: 49)

Yield: 40% m.p.: 76–80° C. (dec)

IR (KBr,cm$^{-1}$): 1637,1513

$^1$HNMR (DMSO d$_6$, 400 MHz) δ: 11.69 (2H,s), 9.59–9.53 (2H,d), 9.19 (2H,m), 9.05 (1H,d), 8.46–8.43 (1H,t),8.34 (1H,d), 8.27–8.23 (4H,m), 7.45–7.41 (2H,m), 6.56 (2H,s), 6.48 (2H,s), 2.81 (3H,s).

Mass (m/z): 505,506,507.

EXAMPLE 51

Pyridinium, 3-[[2-[(1-methylethyl)sulfonyl]hydrazino]carbonyl]-1-[2-oxo-2-(2-thienyl)ethyl]-, bromide (Compound No: 50)

Yield: 70% m.p.: 90–95° C. (dec)

IR (KBr,cm$^{-1}$): 1638,1589

$^1$HNMR (DMSO d$_6$, 400 MHz) δ: 11.27 (1H,s) ,9.91 (1H,s), 9.60 (1H,s), 9.19–9.15 (2H,m), 8.42–8.36 (1H,m) ,8.25–8.21 (2H,m) ,7.43–7.41 (1H,t), 6.45 (2H,s), 1.35–1.34 (6H,d).

Mass (m/z): 368,369,370

EXAMPLE 52

Pyridinium, 3-[[2-(methylsulfonyl)hydrazino]carbonyl]-1-[2-oxo-2-[4-(phenylmethyl)-1-piperidinyl]ethyl]-, chloride (Compound No: 51)

Yield: 17% m.p.: 76–78° C.

IR (KBr,cm$^{-1}$): 1684,1650,1556,1540.

$^1$HNMR (DMSO d$_6$, 400 MHz) δ: 11.46 (1H,s), 9.55 (1H,s), 9.46 (1H,s), 9.09–9.03 (2H,m), 8.36–8.32 (1H,t), 7.33–7.29 (2H,m), 7.23–7.19 (3H,m), 5.88–5.79 (2H,m), 4.30–4.27 (1H,d), 3.76–3.73 (1H,d), 3.10 (4H,m), 2.64 (1H,t), 2.57–2.55 (2H,d), 1.85 (1H,bs), 1.72–1.63 (2H,t), 1.36–1.28 (1H,q), 1.13–1.03 (1H,m)

Mass (m/z): 431,432,433

EXAMPLE 53

Pyridinium, 1-[2-[2-(ethoxycarbonyl)-1-pyrrolidinyl]-2-oxoethyl]-3-[[2-(methylsulfonyl)hydrazino]carbonyl]-, chloride (Compound No: 52)

Yield: 14% m.p.: 88–91° C.

IR (KBr,cm$^{-1}$): 1735,1665,1539

$^1$HNMR (DMSO d$_6$, 400 MHz) δ: 11.48 (1 H,s), 9.96 (1H,s), 9.46 (1H,s), 9.09–9.05 (2H,m), 8.38–8.34 (1H,t), 5.94–5.80 (2H,q), 4.37–4.36 (1H,d), 4.08–4.06 (2H,d), 3.68–3.65 (2H,m), 3.09 (4H,m), 2.23–2.18 (2H,m), 2.04–1.93 (3H,m), 1.18–1.09 (3H,t)

Mass (m/z): 399,400,401

EXAMPLE 54

Pyridinium, 3-bromo-5-[[2-(methylsulfonyl)hydrazino]carbonyl]-1-[2-oxo-2-(2-thienyl)ethyl]-, bromide (Compound No: 53)

Yield: 54% m.p.: Above 190–195° C.(dec)

IR (KBr,cm$^{-1}$): 1682,1557,1540,1520

$^1$HNMR (DMSO d$_6$, 400 MHz) δ: 11.35 (1H,s),10.01 (1H,s), 9.57–9.54 (2H,d), 9.32 (1H,s), 8.26–8.22 (2H,m), 7.42 (1H,s), 6.39 (2H,s), 3.08 (3H,s)

Mass (m/z): 418,419,420

EXAMPLE 55

Pyridinium, 3-[[2-(ethoxycarbonyl)hydrazino]carbonyl]-1-[2-oxo-2-(2-thienyl)ethyl]-, bromide (Compound No: 54)

Yield: 69% m.p.: 155–157° C.

IR (KBr,cm$^{-1}$): 1731,1665,1637

$^1$HNMR (DMSO d$_6$, 400 MHz) δ: 11.04 (1H,s), 9.59 (1H,s), 9.53 (1H,s), 9.18 (1H,s), 9.05–9.04 (1H,d), 8.42 (1H,s), 8.25–8.23 (2H,m), 7.43 (1H,s), 6.46 (2H,s), 4.12–4.11 (2H,s), 1.23 (3H,s)

Mass (m/z): 334,335,336

EXAMPLE 56

Pyridinium, 1-[2-(5-chloro-2-thienyl)-2-oxoethyl]-3-[[2-(methylsulfonyl)hydrazino]carbonyl]-, bromide (Compound No: 55)

Yield: 87% m.p.: 228–230° C.

IR (KBr,cm$^{-1}$): 1708,1664,1631,1550

$^1$HNMR (DMSO d$_6$, 400 MHz) δ: 11.40 (1H,s), 9.98 (1H,s), 9.50 (1 H,s), 9.15 (1H,d), 9.06 (1H,d), 8.43–8.39 (1H,t), 8.16–8.15 (1H,d), 7.51–7.50 (1H,d), 6.41(2H,s), 3.09 (3H,s)

Mass (m/z): 374,375,376,377

EXAMPLE 57

Pyridinium, 3,3'-(hydrazodicarbonyl)bis[1-[2-(4-nitro-2-thienyl)-2-oxoethyl]-, dichloride (Compound No: 56)

Yield: 27% m.p.: 204–207° C.

IR (KBr,cm$^{-1}$): 1681,1539,1514

$^1$HNMR (DMSO d$_6$, 400 MHz) δ: 11.90 (2H,s), 9.63 (2H,s), 9.31–9.30 (4H,m), 9.24–9.22 (2H,m), 8.87 (2H,s), 8.49–8.46 (2H,t), 6.56 (4H,s)

Mass (m/z): 581,582,583

EXAMPLE 58

Pyridinium, 2-methyl-5-[[2-(methylsulfonyl)hydrazino]carbonyl]-1-[2-oxo-2-(2-thienyl)ethyl]-, bromide (Compound No: 57)

Yield: 14% m.p.: 90–95° C.(dec)

IR (KBr,cm$^{-1}$): 1677,1575

$^1$HNMR (DMSO d$_6$, 400 MHz) δ: 11.32 (1H,s), 9.97 (1H,s), 9.52(1H,s), 8.94–8.92 (1H,d), 8.32–8.24 (3H,m), 7.44 (1H,t), 6.54 (2H,s), 3.08 (3H,s), 2.79 (3H,s)

Mass (m/z): 354,355,356

EXAMPLE 59

Pyridinium, 3,3'-(hydrazodicarbonyl)bis[1-[2-(5-methyl-2-thienyl)-2-oxoethyl]-, dichloride (Compound No: 58)

Yield: 37% m.p.: Above 166–168° C.(dec)

IR (KBr,cm$^{-1}$): 1666,1500

$^1$HNMR (DMSO d$_6$, 400 MHz) δ: 11.73 (2H,s), 9.59 (2H,s), 9.19–9.15 (4H,d), 8.45–8.42 (2H,t), 8.06–8.05 (2H,d), 7.15–7.14 (2H,d), 6.43 (4H,s), 2.59 (6H,s)

Mass (m/z): 519,520,521,522

EXAMPLE 60

Pyridinium, 3,3'-(hydrazodicarbonyl)bis[1-[2-[2-(ethoxy carbonyl)-1-pyrrolidinyl]-2-oxoethyl]-, dichloride (Compound No: 59)

Yield: 28% m.p.: 118–120° C.

IR (KBr,cm$^{-1}$): 1660,1510

$^1$HNMR (DMSO d$_6$, 400 MHz) δ: 11.75 (2H,s), 9.51 (2H,s), 9.20–9.10 (4H,m), 8.43–8.40 (2H,t), 5.97–5.83 (4H,m), 4.39–4.36 (2H,m), 4.27–4.22 (1 H,q), 4.12–4.05 (4H,m), 3.71–3.63 (4H,m), 3.48–3.40 (1 H,m), 2.26–2.19 (2H,m), 2.05–1.91 (5H,m), 1.30–1.27 (1H,t), 1.19–1.15 (5H,t)

Mass (m/z): 609,610,611

EXAMPLE 61

Pyridinium, 3-(aminocarbonyl)-1-(2-oxo-2-thien-2-yl-ethyl)-5-[[2-[[1-(2-oxo-2-thien-2-yl-ethyl)pyridinium-3-yl]carbonyl]hydrazino]carbonyl]-, dichloride (Compound No: 60)

Yield: 54% m.p.: Above 127–129° C.(dec)

IR (KBr,cm$^{-1}$): 1678,1513

$^1$HNMR (DMSO d$_6$, 400 MHz) δ: 11.86 (2H,s), 9.83–9.64 (4H,t), 9.24–9.23 (2H,s), 8.82 (1H,s), 8.48–8.45 (1H,t), 8.34 (1H,s), 8.26–8.24 (4H,m), 7.44–7.42 (2H,d), 6.52–6.46 (4H,d)

Mass (m/z): 534,535,536

EXAMPLE 62

Pyridinium, 1-[2-[4-(ethoxycarbonyl)-3-thiazolidinyl]-2-oxoethyl]-3-[[2-(methylsulfonyl)hydrazino]carbonyl]-, chloride (Compound No: 61)

Yield: 29% m.p.: 190–192° C.

IR (KBr,cm$^{-1}$): 1673,1541

$^1$HNMR (DMSO d$_6$, 400 MHz) δ: 11.50 (1H,s), 9.55 (1H,s), 9.48 (1H,s), 9.12–9.08 (2H,m), 8.39–8.34 (1H,t), 6.04–5.99 (2H,m), 4.94–4.91 (1H,m), 4.87–4.84 (1H,d), 4.73–4.71 (1H,d), 4.28–4.23 (1H,q), 4.14–4.09 (1H,q), 3.43–3.38 (1H,m), 3.27–3.22 (1H,m), 3.10 (3H,s), 1.30–1.27 (1H,t), 1.20–1.17 (2H,m)

Mass (m/z): 439,440,441

EXAMPLE 63

Pyridinium, 3,3'-(hydrazodicarbonyl)bis[1-[2-(5-chloro-2-thienyl)-2-oxoethyl]-, dichloride (Compound No: 62)

Yield: 35% m.p.: Above 200–205° C. (dec)

IR (KBr,cm$^{-1}$): 1674,1590,1500

$^1$HNMR (DMSO d$_6$, 400 MHz) δ: 11.90 (2H,s), 9.64–9.61 (2H,d), 9.29–9.20 (4H,m), 8.47–8.44 (2H,t), 8.18–8.17 (2H,d), 7.51–7.50 (2H,d), 6.49–6.48 (4H,s)

Mass (m/z): 559,560,561,562,563,564

EXAMPLE 64

Pyridinium, 3-[[2-(methylsulfonyl)hydrazino]carbonyl]-1-[2-(5-methyl-2-thienyl)-2-oxoethyl]-, chloride (Compound No: 63)

Yield: 22% m.p.: 196–198° C.

IR(KBr,cm$^{-1}$): 1689,1657

$^1$HNMR (DMSO d$_6$, 400 MHz) δ: 11.47 (1H,s), 9.98 (1H,s), 9.53(1H,s), 9.17–9.16 (1H,d), 9.09–9.07 (1H,d), 8.42–8.38 (1H,t), 8.06–8.05 (1H,d), 7.15–7.14 (1H,d), 6.41 (2H,s), 3.09 (3H,s), 2.59 (3H,s)

Mass (m/z): 354,355,356,357

EXAMPLE 65

Pyridinium, 3-[[2-(methylsulfonyl)hydrazino]carbonyl]-1-[2-(4-nitro-2-thienyl)-2-oxoethyl]-, bromide (Compound No: 64)

Yield: 52% m.p.: Above 200–205° C.(dec)

IR (KBr,cm$^{-1}$): 1688,1631,1541

$^1$HNMR (DMSO d$_6$, 400 MHz) δ: 11.41 (1H,s), 9.50 (1 H,s), 9.309–9.306 (1H,d), 9.17–9.15 (1H,d), 9.09–9.07 (1H,d), 8.866–8.862 (1H,d), 8.45–8.41 (1H,t), 6.50 (2H,s), 3.09 (3H,s)

Mass (m/z): 385,386,387

EXAMPLE 66

Pyridinium, 1-[2-oxo-2-(phenylamino)ethyl]-3-[(2-phenylhydrazino)carbonyl]-, chloride (Compound No: 65)

Yield: 45% m.p.: 165–167° C.

IR (KBr,cm$^{-1}$): 1679,1626,1600,1497

$^1$HNMR (DMSO d$_6$, 400 MHz) δ: 11.18 (1H,s), 11.10 (1H,s), 9.62 (1 H,s), 9.24–9.22 (1 H,d), 9.17–9.15 (1 H,d), 8.40–8.36 (1 H,t), 8.19 (1H,s), 7.63–7.61 (2H,d), 7.37–7.33 (2H,t), 7.20–7.16 (2H,t), 7.12–7.09 (1H,t), 6.88–6.86 (2H,d), 6.78–6.74 (1H,t), 5.78 (2H,s)

Mass (m/z): 347,348,349

EXAMPLE 67

Pyridinium, 4-[[[2-(benzoyloxy)ethyl]amino]carbonyl]-1-[2-oxo-2-(phenylamino)ethyl]-, chloride (Compound No: 66)

Yield: 40% m.p.: 178–180° C.

IR (KBr,cm$^{-1}$): 1700,1666,1559

$^1$HNMR (DMSO d$_6$, 400 MHz) δ: 11.13 (1H,s), 9.74–9.71 (1H,t), 9.23–9.22 (2H,d), 8.52–8.50 (2H,d), 8.01–7.99 (2H,d), 7.68–7.60 (3H,m), 7.54–7.51 (2H,t), 7.36–7.32 (2H,t), 7.12–7.08 (1H,t), 5.75 (2H,s), 4.47–4.45 (2H,t), 3.77–3.72 (2H,q).

Mass (m/z): 404,405,406

EXAMPLE 68

Pyridinium, 3-[[2-(methylsulfonyl)hydrazino]carbonyl]-1-[2-(5-nitro-2-thienyl)-2-oxoethyl]-, chloride (Compound No: 67)

Yield: 10% m.p.: Above 105–110° C.(dec)

IR (KBr,cm$^{-1}$): 1680,1620

$^1$HNMR (DMSO d$_6$, 400 MHz) δ: 11.48 (1H,s), 9.98 (1H,s), 9.52 (1H,s), 9.16–9.10 (2H,m), 8.45–8.41 (1H,t), 8.35–8.34 (1H,d), 8.25–8.24 (1H,d), 6.50 (2H,s), 3.09 (3H,s).

Mass (m/z): 385,386,387

EXAMPLE 69

Pyridinium, 1-[2-oxo-2-(2-thienyl)ethyl]-3-[[2-[(trifluoromethyl)sulfonyl]hydrazino]carbonyl]-, bromide (Compound No: 68)

Yield: 22% m.p.: 77–79° C.

IR (KBr,cm$^{-1}$): 2960, 1690, 1673, 1591

$^1$HNMR (DMSO d$_6$, 400 MHz) δ: 11.76 (1H,s), 11.27 (1H,s), 9.61 (1H,s), 9.20–9.19 (1H,d), 9.07–9.05 (1H,d), 8.44–8.41 (1H,t), 8.25–8.22 (2H,m), 7.34–7.41 (1H,m), 6.46 (2H,s).

Mass (m/z): 394, 395, 396

EXAMPLE 70

Pyridinium, 1-[2-oxo-2-(2-thienyl)ethyl]-3-[(2-phenylhydrazino)carbonyl]-, bromide (Compound No. 69)

Yield: 10% m.p.: 192–194° C.

IR (KBr,cm$^{-1}$): 1669,1663,1603, $^1$HNMR (DMSO d$_6$, 400 MHz) δ: 10.99 (1H,s), 9.54 (1H,s), 9.17–9.14 (2H,t), 8.44–8.41 (1H,t), 8.25–8.22 (3H,m), 7.43–7.41 (1H,t), 7.20–7.16 (2H,t), 6.87–6.85 (2H,d), 6.79–6.75 (1H,t), 6.46 (2H,s)

Mass (m/z): 338,339,340

EXAMPLE 71

Pyridinium, 3-[[2-[(4-methoxyphenyl)sulfonyl]hydrazino]carbonyl]-1-[2-oxo-2-(2-thienyl)ethyl]-, bromide (Compound No. 70)

Yield: 28% m.p.: 126–128° C.

IR (KBr,cm$^{-1}$): 1672,1653,1596

$^1$HNMR (DMSO d$_6$, 400 MHz) δ: 11.34–11.33 (1H,d), 10.27–10.26 (1H,d), 9.34 (1H,s), 9.13–9.12 (1H,d), 8.94–8.92 (1H,d), 8.38–8.34(1H,t), 8.24–8.19 (2H,m), 7.82–7.75 (2H,m), 7.42–7.40 (1H,t), 7.07–7.04 (2H,d), 6.40 (2H,s), 3.81 (3H,s).

Mass (m/z): 432,433,434

EXAMPLE 72

Pyridinium, 1-(2-ethoxy-2-oxoethyl)-3-[[2-[(phenylamino)carbonyl]hydrazino]carbonyl]-, bromide (Compound No. 71)

Yield: 25% m.p.: 183–185° C.

IR (KBr,cm$^1$): 1746,1717,1682

$^1$HNMR (DMSO d$_6$, 400 MHz) δ: 11.02 (1H,s), 9.57 (1H,s), 9.22–9.21 (1 H,d), 9.11–9.09 (1 H,d), 9.00 (1H,s), 8.57 (1H,s), 8.44–8.41 (1H,m), 7.47–7.45 (2H,d), 7.29–7.25 (2H,t), 7.00–6.96 (1H,t), 5.74 (2H,s), 4.28–4.23 (2H,q), 1.28–1.25 (3H,t).

Mass (m/z): 343,344,345,346

EXAMPLE 73

Pyridinium, 1-(2-ethoxy-2-oxoethyl)-3-[[2-[(4-methylphenyl)sulfonyl]hydrazino]carbonyl]-, bromide (Compound No. 72)

Yield: 54% m.p.: 174–176° C.

IR (KBr,cm$^{-1}$): 1746,1712,1634

$^1$HNMR (DMSO d$_6$, 400 MHz) δ: 11.33 (1H,s), 10.36 (1H,s), 9.37 (1H,s), 9.18–9.16 (1H,d), 8.93–8.91 (1H,d), 8.37–8.33 (1H,t), 7.78–7.76 (2H,d), 7.37–7.35 (2H,d), 5.68 (2H,s), 4.26–4.20 (2H,q), 2.37 (3H,s), 1.27–1.23 (3H,t).

Mass (m/z): 378,379,380,381

EXAMPLE 74

Pyridinium, 1-(2-oxo-2-phenylethyl)-3-[[2-[(phenylamino)carbonyl]hydrazino]carbonyl]-, bromide (Compound No. 73)

Yield: 70% m.p.: 206–208° C.

IR (KBr,cm$^{-1}$): 1713,1684,1634

$^1$HNMR (DMSO d$_6$, 400 MHz) δ: 11.05 (1H,s), 9.55 (1H,s), 9.18–9.13 (2H,m), 9.02 (1H,s), 8.59 (1H,s), 8.49–8.45 (1H,m), 8.09–8.07 (2H,d), 7.84–7.80 (1H,t), 7.71–7.67 (2H,t), 7.49–7.47 (2H,d), 7.30–7.26 (2H,t), 7.01–6.97 (1H,t), 6.56 (2H,s).

Mass (m/z): 375,376,377

EXAMPLE 75

Pyridinium, 1-[2-oxo-2-(phenylamino)ethyl]-3-[[2-[(phenylmethyl)sulfonyl]hydrazino]carbonyl]-, chloride (Compound No. 74)

Yield: 48% m.p.: 208–210° C.

IR (KBr,cm$^{-1}$): 1712,1681,1632

$^1$HNMR (DMSO d$_6$, 400 MHz) δ: 11.46 (1H,s), 10.80 (1H,s), 9.59 (1H,s), 9.22–9.20 (1H,d), 9.08–9.06 (1H,d), 8.38–8.36 (1H,t), 7.60–7.58 (2H,d), 7.49 (2H,m), 7.39–7.34 (5H,m), 7.13–7.10 (1H,t), 5.74(2H,s), 4.52 (2H,s).

Mass (m/z): 425,426,427,428

EXAMPLE 76

Pyridinium, 4-[[2-(methylsulfonyl)hydrazino]carbonyl]-1-(2-oxo-2-phenylethyl)-, bromide (Compound No. 75)

Yield: 10% m.p: 190–192° C.

IR (KBr,cm$^{-1}$): 1679,1630,1650

$^1$HNMR (DMSO d$_6$, 400 MHz) δ: 11.54 (1H,s), 10.03 (1H,s), 9.20–9.18 (2H,d), 8.59–8.57 (2H,d), 8.10–8.08 (2H,d), 7.84–7.80 (1H,t), 7.71–7.67 (2H,t), 6.56 (2H,s), 3.08 (3H,s).

Mass (m/z): 334,335,336

EXAMPLE 77

Pyridinium, 1-(2-oxo-2-phenylethyl)-3-[(2-phenylhydrazino)carbonyl]-, bromide (Compound No. 76)

Yield: 36% m.p.: 204–206° C.

IR (KBr,cm$^{-1}$): 1686,1653,1630

$^1$HNMR (DMSO d$_6$, 400 MHz) δ: 11.01 (1H,s), 9.53 (1H,s), 9.17–9.16 (2H,m), 8.46–8.42 (1H,t), 8.09–8.07 (2H,d), 7.82–7.78 (1H,t), 7.69–7.65 7.65 (2H,t), 7.20–7.16 (2H,t), 6.88–6.86 (2H,d), 6.79–6.75 (1H,t), 6.56 (2H,s)

Mass (m/z): 332,333

EXAMPLE 78

Pyridinium, 4-[[[2-(benzoyloxy)ethyl]amino]carbonyl]-1-(2-ethoxy-2-oxoethyl)-, bromide (Compound No. 77)

Yield: 82% m.p.: 154–156° C.

IR (KBr,cm$^{-1}$): 1742,1719,1707,1675

$^1$HNMR (DMSO d$_6$, 400 MHz) δ: 9.57–9.54 (1H,t), 9.22–9.20 (2H,d), 8.51–8.49 (2H,d), 8.00–7.98 (2H,d), 7.68–7.64 (1H,t), 7.54–7.51 (2H,t), 5.72 (2H,s), 4.47–4.44 (2H,t), 4.27–4.21 (2H,q), 3.76–3.72 (2H,q), 1.27–1.24 (3H,t)

Mass (m/z): 357,358,359.

EXAMPLE 79

Pyridinium, 1-(2-ethoxy-2-oxoethyl)-3-[(2-phenylhydrazino)carbonyl]-, bromide (Compound No. 78)

Yield: 37% m.p.: 185–187° C.

IR (KBr,cm$^{-1}$): 1740,1690,1630.

$^1$HNMR (DMSO d$_6$, 400 MHz) δ: 11.01 (1H,s), 9.58 (1H,s), 9.23–9.14 (2H,m), 8.42–8.39 (1H,t), 8.19 (1H,s), 7.20–7.16 (2H,t), 6.87–6.85 (2H,d), 6.78–6.75 (1H,t), 5.75 (2H,s), 4.28–4.22 (2H,q), 1.28–1.24 (3H,t)

Mass (m/z): 300,301,302.

EXAMPLE 80

Pyridinium, 3-[[2-[(4-methoxyphenyl)sulfonyl]hydrazino]carbonyl]-1-(2-oxo-2-phenylethyl)-, bromide (Compound No. 79)

Yield: 59% m.p.: 188–190° C.

IR (KBr,cm$^{-1}$): 1671,1634,1580.

$^1$HNMR (DMSO d$_6$, 400 MHz) δ: 11.26–11.25 (1H,d), 10.17–10.16 (1H,d), 9.24 (1H,s), 9.03–9.01 (1H,d), 8.87–8.85 (1H,d), 8.31–8.27 (1H,t), 7.97–7.96 (2H,d), 7.74–7.69 (3H,m), 7.60–7.56 (2H,t), 6.99–6.97 (2H,d), 6.40 (2H,s), 3.73 (3H,s).

Mass (m/z): 426,427,428,429

EXAMPLE 81

Pyridinium, 4-[[[2-(benzoyloxy)ethyl]amino]carbonyl]-1-(2-oxo-2-phenylethyl)-, bromide (Compound No. 80)

Yield: 92% m.p.: 202–204° C.

IR (KBr,cm$^{-1}$): 1715,1692,1650

$^1$HNMR (DMSO d$_6$, 400 MHz) δ: 9.55 (1H,s), 9.14–9.13 (2H,d), 8.52–8.51 (2H,d), 8.07–7.99 (4H,m), 7.80–7.51 (6H,m), 6.52 (2H,s), 4.46 (2H,s), 3.76–3.75 (2H,s).

Mass (m/z): 389,390,391,392

EXAMPLE 82

Pyridinium, 1-(2-ethoxy-2-oxoethyl)-4-[[2-(methylsulfonyl)hydrazino]carbonyl]-, bromide (Compound No. 81)

Yield: 45% m.p.: 94–96° C.

IR (KBr,cm$^{-1}$): 1726,1681,1643

$^1$HNMR (DMSO d$_6$, 400 MHz) δ: 11.49 (1H,s), 9.98 (1H,s), 9.23–9.21 (2H,d), 8.54–8.52 (2H,d), 5.73 (2H,s), 4.28–4.22 (2H,q), 3.09 (3H,s), 1.28–1.25 (3H,t).

Mass (m/z): 302,303,304,305.

PHARMACEUTICAL COMPOSITIONS

Pharmaceutical compositions may be prepared with a pharmaceutically effective quantity of compounds of general formula I, individually or in combination. The following pharmaceutical formulations suggested are by way of example alone and in no way restrict the forms in which they can be used.

Oral Formulations

Oral formulations may be administered as solid dosage forms for example pellets, powders, sachets or discreet units such as tablets or capsules and like. Other orally administered pharmaceutical preparations include monophasic and biphasic liquid dosage forms either in ready to use form or forms suitable for reconstitution such as mixtures, syrups, suspensions or emulsions. The preparations in addition may contain diluents, dispersing agents, buffers, stabilizers, solubilizers, surfactants, preservatives, chelating agents and/or other pharmaceutical additives as are used. Aqueous or non aqueous vehicle or their combination may be used and if desired may contain suitable sweetener, flavoring agent or similar substances. In case of suspension or emulsion a suitable thickening agent or suspending agent or emulsifying agent may be present in addition. Alternatively, the compounds may be administered as such in their pure form unassociated with other additives for example as capsules or sachets. It may also be administered with a vehicle. Pharmaceutical preparations can have a slow, delayed or controlled release of active ingredients as is provided by a matrix or diffusion controlled system.

When the present invention or its salts or suitable complexes is presented as a discreet unit dosage form like tablet, it may contain in addition medically inert excipients as are used in the art. Diluents such as starch, lactose, dicalcium phosphate, talc, magnesium stearate, polymeric substances like methyl cellulose, fatty acids and derivatives, sodium starch glycollate, etc. may also be used.

EXAMPLE 83

Preparation of Oral Dosage Form

A typical tablet has the following composition:

Active ingredient of formula I as given above
Lactose 135 mg
Starch 76 mg
Polyvinyl pyrolidone (K-30) 2 mg
Talc 1.5 mg
Magnesium Stearate 1.0 mg
Parenteral Formulations For parenteral administration, the compounds or their salts or suitable complexes thereof may be present in a sterile vehicle which may be an aqueous or non aqueous vehicle or a combination thereof. The examples of vehicles are water, ethyl oleate, oils and derivatives of polyols, glycols and their derivatives. It may contain additives common in injectable preparations like stabilizers, solubilizers, pH modifiers, buffers, antioxidants, cosolvents, complexing agents, tonicity modifiers, etc.

Some suitable additives are for example tartrate, citrate or similar buffers, alcohol, sodium chloride, dextrose and high molecular weight polymers. Another alternative is sterile powder reconstitution. The compound may be administered in the form of injection for more than once daily administration, or intravenous infusion/drip or suitable depot preparation.

EXAMPLE 84

Preparation Suitable for Parenteral Administration has the Following Composition Active ingredient of formula I as given above
Polyethylene glycol (400) 0.75 ml
Sodium metabisulphite 0.01%
Isotonic saline/WFI q.s.
Other Formulations For the dermatological application and for the discoloration of teeth, the recommended formulations are lotions, oral rinse and toothpaste containing appropriate amount of the compounds of the general formula I.

The above examples are presented by way of illustration alone and in no way limit the scope of the invention.

What is claimed is:

1. A compound represented by general formula (I), or a pharmaceutically acceptable salt thereof

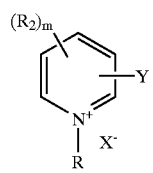

(I)

wherein
Y is —C(O)$R_1$;
$R_1$ is —$R_4$—$R_5$ or —N($R_7$)N($R_7$)$R_9$;
$R_4$ is selected from the group consisting of —N($R_7$)$R_6$O—, —N($R_7$)$R_6$N($R_7$)—, —O$R_6$O—, and —O$R_6$N($R_7$)—, where $R_6$ is alkyl with $C_2$–$C_8$ carbon atoms;
$R_5$ is selected from the group consisting of alkyl, aryl containing up to two conjugated or fused ring systems including heteroaryl, —COR$_7$, —SO$_2$R$_7$, —C(S)NHR$_7$, —C(NH)NHR$_7$, —COR$_{10}$, and —C(O)NHR$_7$ where $R_7$ is selected from the group consisting of H, alkyl and aryl containing up to two conjugated or fused ring systems including heteroaryl, provided $R_7$ may be the same or different for $R_1$ and $R_3$ in the same compound;
$R_2$ is selected from the group consisting of F, Cl, Br, I, OR$_7$, NO$_2$, alkyl, aryl containing up to two conjugated or fused ring systems including heteroaryl, formyl, acyl, C(O)NR$_7$R$_{10}$, C(O)OR$_7$, NR$_7$R$_{10}$, SR$_7$, SO$_2$NH$_2$, SO$_2$alkyl and SO$_2$aryl;
m is 0, 1 or 2;
R is —CH$_2$—C(O)—$R_3$;
$R_3$ is selected from the group consisting of $R_7$, —O-alkyl, —O-aryl, N($R_7$)($R_{10}$), N($R_7$)N($R_7$)($R_{10}$), and CH($R_7$)C(O)$R_8$ where $R_8$ is selected from the group consisting of $R_7$, OR$_7$ and NR$_7$R$_{10}$;
$R_9$ is selected from the group consisting of hydrogen, alkyl, aryl containing up to two conjugated or fused ring systems including heteroaryl, —C(O)R$_{10}$, —SO$_2$R$_{10}$, —C(S)NHR$_{10}$, —C(NH)NH(R$_{10}$) and —C(O)NHR$_{10}$;
$R_{10}$ is selected from the group consisting of H, alkyl and aryl containing up to two conjugated or fused ring systems including heteroaryl and in each case may be the same or different from substituent $R_7$, provided $R_{10}$ may be the same or different for $R_1$ and $R_3$ in the same compound;
X is selected from group consisting of a halide ion, acetate ion, perchlorate ion, sulfonate ion, oxalate ion, citrate ion, tosylate ion, maleate ion, mesylate ion, carbonate ion, sulfite ion, phosphoric hydrogen ion, phosphonate ion, phosphate ion, BF$_4^-$ and PF$_6^-$;
with proviso that,
(i) when two alkyl groups are present on the same carbon or nitrogen, they may be linked together to form a cyclic structure; and
(ii) the nitrogen of heteroaryl ring of $R_{10}$, when present, may be quaternized with a compound X—CH$_2$—C(O)—$R_3$, where X and $R_3$ have the meaning as given above.

2. The compound as claimed in claim 1, wherein —C(O)$R_1$ group is at position 3 or 4.

3. The compound as claimed in claim 2, wherein the position for —C(O)$R_1$ group is at position 3.

4. The compound as claimed in claim 1, wherein m is 0 or 1.

5. The compound as claimed in claim 2, wherein m is 0 or 1.

6. The compound as claimed in claim 3, wherein m is 0 or 1.

7. The compound as claimed in claim 1, wherein m is 0.

8. The compound as claimed in claim 2, wherein m is 0.

9. The compound as claimed in claim 3, wherein m is 0.

10. The compound as claimed in claim 1, wherein X is a halide ion.

11. The compound as claimed in claim 1, which is selected from the group consisting of the following compounds:

(aa) Pyridinium, 3,3'-(hydrazodicarbonyl)bis[1-[2-(2-furanyl)-2-oxoethyl]-, dibromide or a pharmaceutically acceptable salt thereof, (ab) Pyridinium, 3,3'-(hydrazodicarbonyl)bis[1-[2-(2-thienyl)-2-oxoethyl]-, dichloride or a pharmaceutically acceptable salt thereof, (ac) Pyridinium, 3,3'-(hydrazodicarbonyl)bis[1-[2-(cyclopropylamino)-2-oxoethyl]-, dichloride or a pharmaceutically acceptable salt thereof, (ad) Pyridinium, 3-[[(2-methoxyethyl)amino]carbonyl]-1-[2-(2,4-dichlorophenyl)-2-oxoethyl]-, bromide or a pharmaceutically acceptable salt thereof,
(ae) Pyridinium, 3-bromo-5-[[2-(methoxyethyl)amino]carbonyl]-1-[2-oxo-2-(2-thienyl)ethyl]-, chloride or a pharmaceutically acceptable salt thereof,
(af) Pyridinium, 3-[[2-(methylsulfonyl)hydrazino]carbonyl]-1-[2-oxo-2-(2-thienyl)ethyl]-, chloride or a pharmaceutically acceptable salt thereof,
(ag) Pyridinium, 3-[[2-[(2-chloro-3-pyridinyl)carbonyl]hydrazino]carbonyl]-1-[2-oxo-2-(2-thienyl)ethyl]-, chloride or a pharmaceutically acceptable salt thereof,
(ah) Pyridinium, 1-[2-(cyclopropylamino)-2-oxoethyl]-3-[[(2-methoxyethyl)amino]carbonyl]-, chloride or a pharmaceutically acceptable salt thereof,
(ai) Pyridinium, 1-[2-[(1-methylethyl)amino]-2-oxoethyl]-3-[[2-(methylsulfonyl)hydrazino]carbonyl]-, chloride or a pharmaceutically acceptable salt thereof,
(aj) Pyridinium, 3-[[2-(3-cyclohexyl-1-oxopropyl)hydrazino]carbonyl]-1-[2-oxo-2-(phenylamino)ethyl]-, chloride or a pharmaceutically acceptable salt thereof,
(ak) Pyridinium, 3-[[[2-(benzoyloxy)ethyl]amino]carbonyl]-1-[2-oxo-2-(2-thienyl)ethyl]-, bromide, or a pharmaceutically acceptable salt thereof,
(al) Pyridinium, 3-[[[2-(benzoyloxy)ethyl]amino]carbonyl]-1-(4-ethoxy-2,4-dioxobutyl)-, chloride or a pharmaceutically acceptable salt thereof, and
(am) Pyridinium, 3-[[2-[6-(methoxycarbonyl)-3-pyridinyl]carbonyl]hydrazino]carbonyl]-1-[2-oxo-2-(2-thienyl)ethyl]-, chloride or a pharmaceutically acceptable salt thereof.

12. The compound as claimed in claim 1, which is selected from the group consisting of the following compounds:

(an) Pyridinium, 3-(aminocarbonyl)-1-(2-oxo-2-thien-2-yl-ethyl)-5-[[2-[[1-(2-oxo-2-thien-2-yl-ethyl)pyridinium-3-yl]carbonyl]hydrazino]carbonyl]-, dichloride or a pharmaceutically acceptable salt thereof,
(ao) Pyridinium, 1-[2-oxo-2-(2-thienyl)ethyl]-3-[[2-[(trifluoromethyl)sulfonyl]hydrazino]carbonyl]-, bromide or a pharmaceutically acceptable salt thereof,
(ap) Pyridinium, 2-methyl-1-(2-oxo-2-thien-2-yl-ethyl)-5-[[2-[[1-(2-oxo-2-thien-2-yl-ethyl)pyridinium-3-yl]carbonyl]hydrazino]carbonyl]-, dichloride or a pharmaceutically acceptable salt thereof,
(aq) Pyridinium, 3,3'-(hydrazodicarbonyl)bis[1-[2-(5-methyl-2-thienyl)-2-oxoethyl]-, dichloride or a pharmaceutically acceptable salt thereof,
(ar) Pyridinium, 3,3'-(hydrazodicarbonyl)bis[1-[2-(5-chloro-2-thienyl)-2-oxoethyl]-, dichloride or a pharmaceutically acceptable salt thereof,
(as) Pyridinium, 2-methyl-5-[[2-(methylsulfonyl)hydrazino]carbonyl]-1-(2-oxo-2-(2-thienyl)ethyl]-, bromide or a pharmaceutically acceptable salt thereof,
(at) Pyridinium, 3,3'-(hydrazodicarbonyl)bis[1-[2-(4-nitro-2-thienyl)-2-oxoethyl]-, dichloride or a pharmaceutically acceptable salt thereof,
(au) Pyridinium, 1-[2-oxo-2-(phenylamino)ethyl]-3-[(2-phenylhydrazino)carbonyl]-, chloride or a pharmaceutically acceptable salt thereof,
(av) Pyridinium, 3-[[2-(methylsulfonyl)hydrazino]carbonyl]-1-[2-(4-nitro-2-thienyl)-2-oxoethyl]-, bromide or a pharmaceutically acceptable salt thereof,
(aw) Pyridinium, 3-[[2-(methylsulfonyl)hydrazino]carbonyl]-1-[2-(5-nitro-2-thienyl)-2-oxoethyl]-, chloride or a pharmaceutically acceptable salt thereof,
(ax) Pyridinium, 1-[2-(5-chloro-2-thienyl)-2-oxoethyl]-3-[[2-(methylsulfonyl)hydrazino]carbonyl]-, bromide or a pharmaceutically acceptable salt thereof,
(az) Pyridinium, 3-[[2-[(1-methylethyl)sulfonyl]hydrazino]carbonyl]-1-[2-oxo-2-(2-thienyl)ethyl]-, bromide or a pharmaceutically acceptable salt thereof,
(ba) Pyridinium, 3-bromo-5-[[2-(methylsulfonyl)hydrazino]carbonyl]-1-[2-oxo-2-(2-thienyl)ethyl]-, bromide or a pharmaceutically acceptable salt thereof,
(bb) Pyridinium, 1-[2-[2-(ethoxycarbonyl)-1-pyrrolidinyl]-2-oxoethyl]-3-[[2-(methylsulfonyl)hydrazino]carbonyl]-, chloride or a pharmaceutically acceptable salt thereof,
(bc) Pyridinium, 3-[[2-(methylsulfonyl)hydrazino]carbonyl]-1-[2-(5-methyl-2-thienyl)-2-oxoethyl]-, chloride or a pharmaceutically acceptable salt thereof,
(bd) Pyridinium, 1-[2-[4-(ethoxycarbonyl)-3-thiazolidinyl]-2-oxoethyl]-3-[[2-(methylsulfonyl)hydrazino]carbonyl]-, chloride or a pharmaceutically acceptable salt thereof,
(be) Pyridinium, 3-[[2-(methylsulfonyl)hydrazino]carbonyl]-1-[2-oxo-2-[4-(phenylmethyl)-1-piperidinyl]ethyl]-, chloride or a pharmaceutically acceptable salt thereof,
(bf) Pyridinium, 3,3'-(hydrazodicarbonyl)bis[1-[2-[2-(ethoxy carbonyl)-1-pyrrolidinyl]-2-oxoethyl]-, dichloride or a pharmaceutically acceptable salt thereof,
(bg) Pyridinium, 4-[[[2-(benzoyloxy)ethyl]amino]carbonyl]-1-[2-oxo-2-(phenylamino)ethyl]-, chloride or a pharmaceutically acceptable salt thereof,
(bh) Pyridinium, 1-[2-oxo-2-(2-thienyl)ethyl]-3-[(2-phenylhydrazino)carbonyl]-, bromide or a pharmaceutically acceptable salt thereof,
(bi) Pyridinium, 3-[[2-[(4-methoxyphenyl)sulfonyl]hydrazino]carbonyl]-1-[2-oxo-2-(2-thienyl)ethyl]-, bromide or a pharmaceutically acceptable salt thereof,
(bj) Pyridinium, 1-(2-ethoxy-2-oxoethyl)-3-[[2-[(phenylamino)carbonyl]hydrazino]carbonyl]-, bromide or a pharmaceutically acceptable salt thereof,
(bk) Pyridinium, 1-(2-ethoxy-2-oxoethyl)-3-[[2-[(4-methylphenyl)sulfonyl]hydrazino]carbonyl]-, bromide or a pharmaceutically acceptable salt thereof,
(bl) Pyridinium, 1-(2-oxo-2-phenylethyl)-3-[[2-[(phenylamino)carbonyl]hydrazino]carbonyl]-, bromide or a pharmaceutically acceptable salt thereof,
(bm) Pyridinium, 1-[2-oxo-2-(phenylamino)ethyl]-3-[[2-[(phenylmethyl)sulfonyl]hydrazino]carbonyl]-, chloride or a pharmaceutically acceptable salt thereof,
(bn) Pyridinium, 4-[[2-(methylsulfonyl)hydrazino]carbonyl]-1-(2-oxo-2-phenylethyl)-, bromide or a pharmaceutically acceptable salt thereof,
(bo) Pyridinium, 1-(2-oxo-2-phenylethyl)-3-[(2-phenylhydrazino)carbonyl]-, bromide or a pharmaceutically acceptable salt thereof,
(bp) Pyridinium, 4-[[[2-(benzoyloxy)ethyl]amino]carbonyl]-1-(2-ethoxy-2-oxoethyl)-, bromide or a pharmaceutically acceptable salt thereof,
(bq) Pyridinium, 1-(2-ethoxy-2-oxoethyl)-3-[(2-phenylhydrazino)carbonyl]-, bromide or a pharmaceutically acceptable salt thereof,
(br) Pyridinium, 3-[[2-[(4-methoxyphenyl)sulfonyl]hydrazino]carbonyl]-1-(2-oxo-2-phenylethyl)-, bromide or a pharmaceutically acceptable salt thereof,
(bs) Pyridinium, 4-[[[2-(benzoyloxy)ethyl]amino]carbonyl]-1-(2-oxo-2-phenylethyl)-, bromide or a pharmaceutically acceptable salt thereof, and
(bt) Pyridinium, 1-(2-ethoxy-2-oxoethyl)-4-[[2-(methylsulfonyl)hydrazino]carbonyl]-, bromide or a pharmaceutically acceptable salt thereof.

13. A process for the preparation of a compound represented by general formula (I) as claimed in claim 1 or a pharmaceutically acceptable salt thereof, which comprises providing a substituted pyridine having a backbone structure the same as the compound of general formula (I) or a pharmaceutically acceptable salt thereof that is to be prepared, followed by quaternizing the substituted pyridine with a quaternizing reagent in an alcoholic and/or high boiling solvent under reflux for 6–48 hrs. to give the desired compound represented by general formula (I) or a pharmaceutically acceptable salt thereof.

14. A pharmaceutical composition comprising a pharmaceutically effective amount of one or more compounds represented by general formula (I), as defined in claim 1 or pharmaceutically acceptable salt(s) thereof in admixture with a pharmaceutically acceptable carrier, diluent, solvent or excepient.

15. The pharmaceutical composition as claimed in claim 14 in the form of an oral formulation.

16. The pharmaceutical composition as claimed in claim 14, wherein said acceptable carrier, diluent, solvent or excepient is selected from group consisting of starch, lactose, polyvinyl pyrolidone (K-30), talc and magnesium stearate.

17. The pharmaceutical composition as claimed in claim 14 in the form of a parenteral formulation.

18. A method for the preparation of a parenteral formulation as claimed in claim 17, which comprises dissolving one or more compounds represented by general formula (I), as defined in claim 1 or pharmaceutically acceptable salt(s) thereof, in polyethylene glycol 400 and diluting the solution so obtained with an isotonic solution or water to a desired concentration.

19. The pharmaceutical composition as claimed in claim 14 in the form of a lotion, oral rinse and toothpaste.

20. The pharmaceutical composition as claimed in claim 14, wherein said compound is selected from the group consisting of:

(aa) Pyridinium, 3,3'-(hydrazodicarbonyl)bis[1-[2-(2-furanyl)-2-oxoethyl]-, dibromide or a pharmaceutically acceptable salt thereof, (ab) Pyridinium, 3,3'-(hydrazodicarbonyl)bis[1-[2-(2-thienyl)-2-oxoethyl]-, dichloride or a pharmaceutically acceptable salt thereof, (ac) Pyridinium, 3,3'-(hydrazodicarbonyl)bis[1-[2-(cyclopropylamino)-2-oxoethyl]-, dichloride or a pharmaceutically acceptable salt thereof, (ad) Pyridinium, 3-[[(2-methoxyethyl)amino]carbonyl]-1-[2-(2,4-dichlorophenyl)-2-oxoethyl]-, bromide or a pharmaceutically acceptable salt thereof, (ae) Pyridinium, 3-bromo-5-[[2-(methoxyethyl)amino]carbonyl]-1-[2-oxo-2-(2-thienyl)ethyl]-, chloride or a pharmaceutically acceptable salt thereof, (af) Pyridinium, 3-[[2-(methylsulfonyl)hydrazino]carbonyl]-1-[2-oxo-2-(2-thienyl)ethyl]-, chloride or a pharmaceutically acceptable salt thereof, (ag) Pyridinium, 3-[[2-[(2-chloro-3-pyridinyl)carbonyl]hydrazino]carbonyl]-1-[2-oxo-2-(2-thienyl)ethyl]-, chloride or a pharmaceutically acceptable salt thereof, (ah) Pyridinium, 1-[2-(cyclopropylamino)-2-oxoethyl]-3-[[(2-methoxyethyl)amino]carbonyl]-, chloride or a pharmaceutically acceptable salt thereof, (ai) Pyridinium, 1-[2-[(1-methylethyl)amino]-2-oxoethyl]-3-[[2-(methylsulfonyl)hydrazino]carbonyl]-, chloride or a pharmaceutically acceptable salt thereof, (aj) Pyridinium, 3-[[2-(3-cyclohexyl-1-oxopropyl)hydrazino]carbonyl]-1-[2-oxo-2-(phenylamino)ethyl]-, chloride or a pharmaceutically acceptable salt thereof, (ak) Pyridinium, 3-[[[2-(benzoyloxy)ethyl]amino]carbonyl]-1-[2-oxo-2-(2-thienyl)ethyl]-, bromide or a pharmaceutically acceptable salt thereof, (al) Pyridinium, 3-[[[2-(benzoyloxy)ethyl]amino]carbonyl]-1-(4-ethoxy-2,4-dioxobutyl)-, chloride or a pharmaceutically acceptable salt thereof, and (am) Pyridinium, 3-[[2-[[6-(methoxycarbonyl)-3-pyridinyl]carbonyl]hydrazino]carbonyl]-1-[2-oxo-2-(2-thienyl)ethyl]-, chloride or a pharmaceutically acceptable salt thereof.

21. The pharmaceutical composition as claimed in claim 14, wherein said compound is selected from the group consisting of:

(an) Pyridinium, 3-(aminocarbonyl)-1-(2-oxo-2-thien-2-yl-ethyl)-5-[[2-[[1-(2-oxo-2-thien-2-yl-ethyl)pyridinium-3-yl]carbonyl]hydrazino]carbonyl]-, dichloride or a pharmaceutically acceptable salt thereof, (ao) Pyridinium, 1-[2-oxo-2-(2-thienyl)ethyl]-3-[[2-[(trifluoromethyl)sulfonyl]hydrazino]carbonyl]-, bromide or a pharmaceutically acceptable salt thereof, (ap) Pyridinium, 2-methyl-1-(2-oxo-2-thien-2-yl-ethyl)-5-[[2-[[1-(2-oxo-2-thien-2-yl-ethyl)pyridinium-3-yl]carbonyl]hydrazino]carbonyl]-, dichloride or a pharmaceutically acceptable salt thereof, (aq) Pyridinium, 3,3'-(hydrazodicarbonyl)bis[1-[2-(5-methyl-2-thienyl)-2-oxoethyl]-, dichloride or a pharmaceutically acceptable salt thereof, (ar) Pyridinium, 3,3'-(hydrazodicarbonyl)bis[1-[2-(5-chloro-2-thienyl)-2-oxoethyl]-, dichloride or a pharmaceutically acceptable salt thereof, (as) Pyridinium, 2-methyl-5-[[2-(methylsulfonyl)hydrazino]carbonyl]-1-[2-oxo-2-(2-thienyl)ethyl]-, bromide or a pharmaceutically acceptable salt thereof, (at) Pyridinium, 3,3'-(hydrazodicarbonyl)bis[1-[2-(4-nitro-2-thienyl)-2-oxoethyl]-, dichloride or a pharmaceutically acceptable salt thereof, (au) Pyridinium, 1-[2-oxo-2-(phenylamino)ethyl]-3-[(2-phenylhydrazino)carbonyl]-, chloride or a pharmaceutically acceptable salt thereof, (av) Pyridinium, 3-[[2-(methylsulfonyl)hydrazino]carbonyl]-1-[2-(4-nitro-2-thienyl)-2-oxoethyl]-, bromide or a pharmaceutically acceptable salt thereof, (aw) Pyridinium, 3-[[2-(methylsulfonyl)hydrazino]carbonyl]-1-[2-(5-nitro-2-thienyl)-2-oxoethyl]-, chloride or a pharmaceutically acceptable salt thereof, (ax) Pyridinium, 1-[2-(5-chloro-2-thienyl)-2-oxoethyl]-3-[[2-(methylsulfonyl)hydrazino]carbonyl]-, bromide or a pharmaceutically acceptable salt thereof, (az) Pyridinium, 3-[[2-[(1-methylethyl)sulfonyl]hydrazino]carbonyl]-1-[2-oxo-2-(2-thienyl)ethyl]-, bromide or a pharmaceutically acceptable salt thereof, (ba) Pyridinium, 3-bromo-5-[[2-(methylsulfonyl)hydrazino]carbonyl]-1-[2-oxo-2-(2-thienyl)ethyl]-, bromide or a pharmaceutically acceptable salt thereof, (bb) Pyridinium, 1-[2-[2-(ethoxycarbonyl)-1-pyrrolidinyl]-2-oxoethyl]-3-[[2-(methylsulfonyl)hydrazino]carbonyl]-, chloride or a pharmaceutically acceptable salt thereof, (bc) Pyridinium, 3-[[2-(methylsulfonyl)hydrazino]carbonyl]-1-[2-(5-methyl-2-thienyl)-2-oxoethyl]-, chloride or a pharmaceutically acceptable salt thereof, (bd) Pyridinium, 1-[2-[4-(ethoxycarbonyl)-3-thiazolidinyl]-2-oxoethyl]-3-[[2-(methylsulfonyl)hydrazino]carbonyl]-, chloride or a pharmaceutically acceptable salt thereof, (be) Pyridinium, 3-[[2-(methylsulfonyl)hydrazino]carbonyl]-1-[2-oxo-2-[4-(phenylmethyl)-1-piperidinyl]ethyl]-, chloride or a pharmaceutically acceptable salt thereof, (bf) Pyridinium, 3,3'-(hydrazodicarbonyl)bis[1-[2-[2-(ethoxy carbonyl)-1-pyrrolidinyl]-2-oxoethyl]-, dichloride or a pharmaceutically acceptable salt thereof, (bg) Pyridinium, 4-[[[2-(benzoyloxy)ethyl]amino]carbonyl]-1-[2-oxo-2-(phenylamino)ethyl]-, chloride or a pharmaceutically acceptable salt thereof, (bh) Pyridinium, 1-[2-oxo-2-(2-thienyl)ethyl]-3-[(2-phenylhydrazino)carbonyl]-, bromide or a pharmaceutically acceptable salt thereof, (bi) Pyridinium, 3-[[2-[(4-methoxyphenyl)sulfonyl]hydrazino]carbonyl]-1-[2-oxo-2-(2-thienyl)ethyl]-, bromide or a pharmaceutically acceptable salt thereof, (bj) Pyridinium, 1-(2-ethoxy-2-oxoethyl)-3-[[2-[(phenylamino)carbonyl]hydrazino]carbonyl]-, bromide or a pharmaceutically acceptable salt thereof, (bk) Pyridinium, 1-(2-ethoxy-2-oxoethyl)-3-[[2-[(4-methylphenyl)sulfonyl]hydrazino]carbonyl]-, bromide or a pharmaceutically acceptable salt thereof, (bl) Pyridinium, 1-(2-oxo-2-phenylethyl)-3-[[2-[(phenylamino)carbonyl]hydrazino]carbonyl]-, bromide or a pharmaceutically acceptable salt thereof, (bm) Pyridinium, 1-[2-oxo-2-(phenylamino)ethyl]-3-[[2-[(phenylmethyl)sulfonyl]hydrazino]carbonyl]-, chloride or a pharmaceutically acceptable salt thereof, (bn) Pyridinium, 4-[[2-(methylsulfonyl)hydrazino]carbonyl]-1-(2-oxo-2-phenylethyl)-, bromide or a pharmaceutically acceptable salt thereof, (bo) Pyridinium, 1-(2-oxo-2-phenylethyl)-3-[(2-phenylhydrazino)carbonyl]-, bromide or a pharmaceutically acceptable salt thereof, (bp) Pyridinium, 4-[[[2-(benzoyloxy)ethyl]amino]carbonyl]-1-(2-ethoxy-2-oxoethyl)-, bromide or a pharmaceutically acceptable salt thereof, (bq) Pyridinium, 1-(2-ethoxy-2-oxoethyl)-3-[(2-phenylhydrazino)carbonyl]-, bromide or a pharmaceutically acceptable salt thereof, (br) Pyridinium, 3-[[2-[(4-methoxyphenyl)sulfonyl]hydrazino]carbonyl]-1-(2-oxo-2-phenylethyl)-, bromide or a pharmaceutically acceptable salt thereof, (bs) Pyridinium, 4-[[[2-(benzoyloxy)ethyl]amino]carbonyl]-1-(2-oxo-2-phenylethyl)-, bromide or a pharmaceutically acceptable salt thereof, and (bt) Pyridinium, 1-(2-ethoxy-2-oxoethyl)-4-[[2-(methylsulfonyl)hydrazino]carbonyl]-, bromide or a pharmaceutically acceptable salt thereof.

22. A method for treating a diabetic patient by breaking a preformed AGE, within said patient, which comprises, administering an effective amount of a compound represented by general formula (I) as claimed in claim 1 or a pharmaceutically acceptable salt thereof, either singly or in combination with other drugs for antidiabetic therapy.

23. A method of preventing or treating diseases caused by diabetes and aging related complications including vascular and neuro-vascular complications, which comprises, administering to a patient in need thereof, an effective amount of a compound represented by general formula (I) as claimed in claim 1 or a pharmaceutically acceptable salt thereof, either singly or in combination with a pharmaceutically acceptable carrier, diluent or excepient.

24. The method as claimed in claim 23, wherein the disease prevented or treated is a nephrological disorder, neurological disorder, atherosclerosis, retinal disorder, dermatological disorder, non-enzymatic browning of oral cavity, endothelial or other organ dysfunction and growth impairment.

25. The method as claimed in claim 23, wherein the disease prevented or treated is an inflammatory disorder, immunological disorder, or oxidative stress.

26. The method as claimed in claim 22, wherein said compound is selected from the group consisting of:

(aa) Pyridinium, 3,3'-(hydrazodicarbonyl)bis[1-[2-(2-furanyl)-2-oxoethyl]-, dibromide or a pharmaceutically acceptable salt thereof, (ab) Pyridinium, 3,3'-(hydrazodicarbonyl)bis[1-[2-(2-thienyl)-2-oxoethyl]-, dichloride or a pharmaceutically acceptable salt thereof, (ac) Pyridinium, 3,3'-(hydrazodicarbonyl)bis[1-[2-(cyclopropylamino)-2-oxoethyl]-, dichloride or a pharmaceutically acceptable salt thereof, (ad) Pyridinium, 3-[[(2-methoxyethyl)amino]carbonyl]-1-[2-(2,4-dichlorophenyl)-2-oxoethyl]-, bromide or a pharmaceutically acceptable salt thereof, (ae) Pyridinium, 3-bromo-5-[[2-(methoxyethyl)amino]carbonyl]-1-[2-oxo-2-(2-thienyl)ethyl]-, chloride or a pharmaceutically acceptable salt thereof, (af) Pyridinium, 3-[[2-(methylsulfonyl)hydrazino]carbonyl]-1-[2-oxo-2-(2-thienyl)ethyl]-, chloride or a pharmaceutically acceptable salt thereof, (ag) Pyridinium, 3-[[2-[(2-chloro-3-pyridinyl)carbonyl]hydrazino]carbonyl]-1-[2-oxo-2-(2-thienyl)ethyl]-, chloride or a pharmaceutically acceptable salt thereof, (ah) Pyridinium, 1-[2-(cyclopropylamino)-2-oxoethyl]-3-[[(2-methoxyethyl)amino]carbonyl]-, chloride or a pharmaceutically acceptable salt thereof, (ai) Pyridinium, 1-[2-[(1-methylethyl)amino]-2-oxoethyl]-3-[[2-(methylsulfonyl)hydrazino]carbonyl]-, chloride or a pharmaceutically acceptable salt thereof, (aj) Pyridinium, 3-[[2-(3-cyclohexyl-1-oxopropyl)hydrazino]carbonyl]-1-[2-oxo-2-(phenylamino)ethyl]-, chloride or a pharmaceutically acceptable salt thereof, (ak) Pyridinium, 3-[[[2-(benzoyloxy)ethyl]amino]carbonyl]-1-[2-oxo-2-(2-thienyl)ethyl]-, bromide or a pharmaceutically acceptable salt thereof, (al) Pyridinium, 3-[[[2-(benzoyloxy)ethyl]amino]carbonyl]-1-(4-ethoxy-2,4-dioxobutyl)-, chloride or a pharmaceutically acceptable salt thereof, and (am) Pyridinium, 3-[[2-[[6-(methoxycarbonyl)-3-pyridinyl]carbonyl]hydrazino]carbonyl]-1-[2-oxo-2-(2-thienyl)ethyl]-, chloride or a pharmaceutically acceptable salt thereof.

27. The method as claimed in claim 22, wherein said compound is selected from the group consisting of:

(an) Pyridinium, 3-(aminocarbonyl)-1-(2-oxo-2-thien-2-yl-ethyl)-5-[[2-[[1-(2-oxo-2-thien-2-yl-ethyl)pyridinium-3-yl]carbonyl]hydrazino]carbonyl]-, dichloride or a pharmaceutically acceptable salt thereof, (ao) Pyridinium, 1-[2-oxo-2-(2-thienyl)ethyl]-3-[[2-[(trifluoromethyl)sulfonyl]hydrazino]carbonyl]-, bromide or a pharmaceutically acceptable salt thereof, (ap) Pyridinium, 2-methyl-1-(2-oxo-2-thien-2-yl-ethyl)-5-[[2-[[1-(2-oxo-2-thien-2-yl-ethyl)pyridinium-3-yl]carbonyl]hydrazino]carbonyl]-, dichloride or a pharmaceutically acceptable salt thereof, (aq) Pyridinium, 3,3'-(hydrazodicarbonyl)bis[1-[2-(5-methyl-2-thienyl)-2-oxoethyl]-, dichloride or a pharmaceutically acceptable salt thereof, (ar) Pyridinium, 3,3'-(hydrazodicarbonyl)bis[1-[2-(5-chloro-2-thienyl)-2-oxoethyl]-, dichloride or a pharmaceutically acceptable salt thereof, (as) Pyridinium, 2-methyl-5-[[2-(methylsulfonyl)hydrazino]carbonyl]-1-[2-oxo-2-(2-thienyl)ethyl]-, bromide or a pharmaceutically acceptable salt thereof, (at) Pyridinium, 3,3'-(hydrazodicarbonyl)bis[1-[2-(4-nitro-2-thienyl)-2-oxoethyl]-, dichloride or a pharmaceutically acceptable salt thereof, (au) Pyridinium, 1-[2-oxo-2-(phenylamino)ethyl]-3-[(2-phenylhydrazino)carbonyl]-, chloride or a pharmaceutically acceptable salt thereof,
(av) Pyridinium, 3-[[2-(methylsulfonyl)hydrazino]carbonyl]-1-[2-(4-nitro-2-thienyl)-2-oxoethyl]-, bromide or a pharmaceutically acceptable salt thereof,
(aw) Pyridinium, 3-[[2-(methylsulfonyl)hydrazino]carbonyl]-1-[2-(5-nitro-2-thienyl)-2-oxoethyl]-, chloride or a pharmaceutically acceptable salt thereof,
(ax) Pyridinium, 1-[2-(5-chloro-2-thienyl)-2-oxoethyl]-3-[[2-(methylsulfonyl)hydrazino]carbonyl]-, bromide or a pharmaceutically acceptable salt thereof,
(az) Pyridinium, 3-[[2-[(1-methylethyl)sulfonyl]hydrazino]carbonyl]-1-[2-oxo-2-(2-thienyl)ethyl]-, bromide or a pharmaceutically acceptable salt thereof,
(ba) Pyridinium, 3-bromo-5-[[2-(methylsulfonyl)hydrazino]carbonyl]-1-[2-oxo-2-(2-thienyl)ethyl]-, bromide or a pharmaceutically acceptable salt thereof,
(bb) Pyridinium, 1-[2-[2-(ethoxycarbonyl)-1-pyrrolidinyl]-2-oxoethyl]-3-[[2-(methylsulfonyl)hydrazino]carbonyl]-, chloride or a pharmaceutically acceptable salt thereof,
(bc) Pyridinium, 3-[[2-(methylsulfonyl)hydrazino]carbonyl]-1-[2-(5-methyl-2-thienyl)-2-oxoethyl]-, chloride or a pharmaceutically acceptable salt thereof,
(bd) Pyridinium, 1-[2-[4-(ethoxycarbonyl)-3-thiazolidinyl]-2-oxoethyl]-3-[[2-(methylsulfonyl)hydrazino]carbonyl]-, chloride or a pharmaceutically acceptable salt thereof,
(be) Pyridinium, 3-[[2-(methylsulfonyl)hydrazino]carbonyl]-1-[2-oxo-2-[4-(phenylmethyl)-1-piperidinyl]ethyl]-, chloride or a pharmaceutically acceptable salt thereof,
(bf) Pyridinium, 3,3'-(hydrazodicarbonyl)bis[1-[2-[2-(ethoxy carbonyl)-1-pyrrolidinyl]-2-oxoethyl]-, dichloride or a pharmaceutically acceptable salt thereof,
(bg) Pyridinium, 4-[[[2-(benzoyloxy)ethyl]amino]carbonyl]-1-[2-oxo-2-(phenylamino)ethyl]-, chloride or a pharmaceutically acceptable salt thereof,
(bh) Pyridinium, 1-[2-oxo-2-(2-thienyl)ethyl]-3-[(2-phenylhydrazino)carbonyl]-, bromide or a pharmaceutically acceptable salt thereof,
(bi) Pyridinium, 3-[[2-[(4-methoxyphenyl)sulfonyl]hydrazino]carbonyl]-1-[2-oxo-2-(2-thienyl)ethyl]-, bromide or a pharmaceutically acceptable salt thereof,
(bj) Pyridinium, 1-(2-ethoxy-2-oxoethyl)-3-[[2-[(phenylamino)carbonyl]hydrazino]carbonyl]-, bromide or a pharmaceutically acceptable salt thereof,
(bk) Pyridinium, 1-(2-ethoxy-2-oxoethyl)-3-[[2-[(4-methylphenyl)sulfonyl]hydrazino]carbonyl]-, bromide or a pharmaceutically acceptable salt thereof,
(bl) Pyridinium, 1-(2-oxo-2-phenylethyl)-3-[[2-[(phenylamino)carbonyl]hydrazino]carbonyl]-, bromide or a pharmaceutically acceptable salt thereof,
(bm) Pyridinium, 1-[2-oxo-2-(phenylamino)ethyl]-3-[[2-[(phenylmethyl)sulfonyl]hydrazino]carbonyl]-, chloride or a pharmaceutically acceptable salt thereof,
(bn) Pyridinium, 4-[[2-(methylsulfonyl)hydrazino]carbonyl]-1-(2-oxo-2-phenylethyl)-, bromide or a pharmaceutically acceptable salt thereof,
(bo) Pyridinium, 1-(2-oxo-2-phenylethyl)-3-[(2-phenylhydrazino)carbonyl]-, bromide or a pharmaceutically acceptable salt thereof,
(bp) Pyridinium, 4-[[[2-(benzoyloxy)ethyl]amino]carbonyl]-1-(2-ethoxy-2-oxoethyl)-, bromide or a pharmaceutically acceptable salt thereof,
(bq) Pyridinium, 1-(2-ethoxy-2-oxoethyl)-3-[(2-phenylhydrazino)carbonyl]-, bromide or a pharmaceutically acceptable salt thereof,
(br) Pyridinium, 3-[[2-[(4-methoxyphenyl)sulfonyl]hydrazino]carbonyl]-1-(2-oxo-2-phenylethyl)-, bromide or a pharmaceutically acceptable salt thereof,
(bs) Pyridinium, 4-[[[2-(benzoyloxy)ethyl]amino]carbonyl]-1-(2-oxo-2-phenylethyl)-, bromide or a pharmaceutically acceptable salt thereof and
(bt) Pyridinium, 1-(2-ethoxy-2-oxoethyl)-4-[[2-(methylsulfonyl)hydrazino]carbonyl]-, bromide or a pharmaceutically acceptable salt thereof.

28. The method as claimed in claim 23, wherein said compound is selected from the group consisting of:

(aa) Pyridinium, 3,3'-(hydrazodicarbonyl)bis[1-[2-(2-furanyl)-2-oxoethyl]-, dibromide or a pharmaceutically acceptable salt thereof,
(ab) Pyridinium, 3,3'-(hydrazodicarbonyl)bis[1-[2-(2-thienyl)-2-oxoethyl]-, dichloride or a pharmaceutically acceptable salt thereof,
(ac) Pyridinium, 3,3'-(hydrazodicarbonyl)bis[1-[2-(cyclopropylamino)-2-oxoethyl]-, dichloride or a pharmaceutically acceptable salt thereof,
(ad) Pyridinium, 3-[[(2-methoxyethyl)amino]carbonyl]-1-[2-(2,4-dichlorophenyl)-2-oxoethyl]-, bromide or a pharmaceutically acceptable salt thereof,
(ae) Pyridinium, 3-bromo-5-[[2-(methoxyethyl)amino]carbonyl]-1-[2-oxo-2-(2-thienyl)ethyl]-, chloride or a pharmaceutically acceptable salt thereof,
(af) Pyridinium, 3-[[2-(methylsulfonyl)hydrazino]carbonyl]-1-[2-oxo-2-(2-thienyl)ethyl]-, chloride or a pharmaceutically acceptable salt thereof,
(ag) Pyridinium, 3-[[2-[(2-chloro-3-pyridinyl)carbonyl]hydrazino]carbonyl]-1-[2-oxo-2-(2-thienyl)ethyl]-, chloride or a pharmaceutically acceptable salt thereof,
(ah) Pyridinium, 1-[2-(cyclopropylamino)-2-oxoethyl]-3-[[(2-methoxyethyl)amino]carbonyl]-, chloride or a pharmaceutically acceptable salt thereof,
(ai) Pyridinium, 1-[2-[(1-methylethyl)amino]-2-oxoethyl]-3-[[2-(methylsulfonyl)hydrazino]carbonyl]-, chloride or a pharmaceutically acceptable salt thereof,
(aj) Pyridinium, 3-[[2-(3-cyclohexyl-1-oxopropyl)hydrazino]carbonyl]-1-[2-oxo-2-(phenylamino)ethyl]-, chloride or a pharmaceutically acceptable salt thereof,
(ak) Pyridinium, 3-[[[2-(benzoyloxy)ethyl]amino]carbonyl]-1-[2-oxo-2-(2-thienyl)ethyl]-, bromide or a pharmaceutically acceptable salt thereof,
(al) Pyridinium, 3-[[[2-(benzoyloxy)ethyl]amino]carbonyl]-1-(4-ethoxy-2,4-dioxobutyl)-, chloride or a pharmaceutically acceptable salt thereof, and
(am) Pyridinium, 3-[[2-[[6-(methoxycarbonyl)-3-pyridinyl]carbonyl]hydrazino]carbonyl]-1-[2-oxo-2-(2-thienyl)ethyl]-, chloride or a pharmaceutically acceptable salt thereof.

29. The method as claimed in claim 23, wherein said compound is selected from the group consisting of:

(an) Pyridinium, 3-(aminocarbonyl)-1-(2-oxo-2-thien-2-yl-ethyl)-5-[[2-[[1-(2-oxo-2-thien-2-yl-ethyl)pyridinium-3-yl]carbonyl]hydrazino]carbonyl]-, dichloride or a pharmaceutically acceptable salt thereof,
(ao) Pyridinium, 1-[2-oxo-2-(2-thienyl)ethyl]-3-[[2-[(trifluoromethyl)sulfonyl]hydrazino]carbonyl]-, bromide or a pharmaceutically acceptable salt thereof,
(ap) Pyridinium, 2-methyl-1-(2-oxo-2-thien-2-yl-ethyl)-5-[[2-[[1-(2-oxo-2-thien-2-yl-ethyl)pyridinium-3-yl]carbonyl]hydrazino]carbonyl]-, dichloride or a pharmaceutically acceptable salt thereof,
(aq) Pyridinium, 3,3'-(hydrazodicarbonyl)bis[1-[2-(5-methyl-2-thienyl)-2-oxoethyl]-, dichloride or a pharmaceutically acceptable salt thereof, (ar) Pyridinium, 3,3'-(hydrazodicarbonyl)bis[1-[2-(5-chloro-2-thienyl)-2-oxoethyl]-, dichloride or a pharmaceutically acceptable salt thereof,
(as) Pyridinium, 2-methyl-5-[[2-(methylsulfonyl)hydrazino]carbonyl]-1-[2-oxo-2-(2-thienyl)ethyl]-, bromide or a pharmaceutically acceptable salt thereof,
(at) Pyridinium, 3,3'-(hydrazodicarbonyl)bis[1-[2-(4-nitro-2-thienyl)-2-oxoethyl]-, dichloride or a pharmaceutically acceptable salt thereof,
(au) Pyridinium, 1-[2-oxo-2-(phenylamino)ethyl]-3-[(2-phenylhydrazino)carbonyl]-, chloride or a pharmaceutically acceptable salt thereof,
(av) Pyridinium, 3-[[2-(methylsulfonyl)hydrazino]carbonyl]-1-[2-(4-nitro-2-thienyl)-2-oxoethyl]-, bromide or a pharmaceutically acceptable salt thereof,
(aw) Pyridinium, 3-[[2-(methylsulfonyl)hydrazino]carbonyl]-1-[2-(5-nitro-2-thienyl)-2-oxoethyl]-, chloride or a pharmaceutically acceptable salt thereof,
(ax) Pyridinium, 1-[2-(5-chloro-2-thienyl)-2-oxoethyl]-3-[[2-(methylsulfonyl)hydrazino]carbonyl]-, bromide or a pharmaceutically acceptable salt thereof,
(az) Pyridinium, 3-[[2-[(1-methylethyl)sulfonyl]hydrazino]carbonyl]-1-[2-oxo-2-(2-thienyl)ethyl]-, bromide or a pharmaceutically acceptable salt thereof,
(ba) Pyridinium, 3-bromo-5-[[2-(methylsulfonyl)hydrazino]carbonyl]-1-[2-oxo-2-(2-thienyl)ethyl]-, bromide or a pharmaceutically acceptable salt thereof,
(bb) Pyridinium, 1-[2-[2-(ethoxycarbonyl)-1-pyrrolidinyl]-2-oxoethyl]-3-[[2-(methylsulfonyl)hydrazino]carbonyl]-, chloride or a pharmaceutically acceptable salt thereof,
(bc) Pyridinium, 3-[[2-(methylsulfonyl)hydrazino]carbonyl]-1-[2-(5-methyl-2-thienyl)-2-oxoethyl]-, chloride or a pharmaceutically acceptable salt thereof,
(bd) Pyridinium, 1-[2-[4-(ethoxycarbonyl)-3-thiazolidinyl]-2-oxoethyl]-3-[[2-(methylsulfonyl)hydrazino]carbonyl]-, chloride or a pharmaceutically acceptable salt thereof,
(be) Pyridinium, 3-[[2-(methylsulfonyl)hydrazino]carbonyl]-1-[2-oxo-2-[4-(phenylmethyl)-1-piperidinyl]ethyl]-, chloride or a pharmaceutically acceptable salt thereof,
(bf) Pyridinium, 3,3'-(hydrazodicarbonyl)bis[1-[2-[2-(ethoxy carbonyl)-1-pyrrolidinyl]-2-oxoethyl]-, dichloride or a pharmaceutically acceptable salt thereof,
(bg) Pyridinium, 4-[[[2-(benzoyloxy)ethyl]amino]carbonyl]-1-[2-oxo-2-(phenylamino)ethyl]-, chloride or a pharmaceutically acceptable salt thereof,
(bh) Pyridinium, 1-[2-oxo-2-(2-thienyl)ethyl]-3-[(2-phenylhydrazino)carbonyl]-, bromide or a pharmaceutically acceptable salt thereof,
(bi) Pyridinium, 3-[[2-[(4-methoxyphenyl)sulfonyl]hydrazino]carbonyl]-1-[2-oxo-2-(2-thienyl)ethyl]-, bromide or a pharmaceutically acceptable salt thereof,
(bj) Pyridinium, 1-(2-ethoxy-2-oxoethyl)-3-[[2-[(phenylamino)carbonyl]hydrazino]carbonyl]-, bromide or a pharmaceutically acceptable salt thereof,
(bk) Pyridinium, 1-(2-ethoxy-2-oxoethyl)-3-[[2-[(4-methylphenyl)sulfonyl]hydrazino]carbonyl]-, bromide or a pharmaceutically acceptable salt thereof,
(bl) Pyridinium, 1-(2-oxo-2-phenylethyl)-3-[[2-[(phenylamino)carbonyl]hydrazino]carbonyl]-, bromide or a pharmaceutically acceptable salt thereof,
(bm) Pyridinium, 1-[2-oxo-2-(phenylamino)ethyl]-3-[[2-[(phenylmethyl)sulfonyl]hydrazino]carbonyl]-, chloride or a pharmaceutically acceptable salt thereof,
(bn) Pyridinium, 4-[[2-(methylsulfonyl)hydrazino]carbonyl]-1-(2-oxo-2-phenylethyl)-, bromide or a pharmaceutically acceptable salt thereof,
(bo) Pyridinium, 1-(2-oxo-2-phenylethyl)-3-[(2-phenylhydrazino)carbonyl]-, bromide or a pharmaceutically acceptable salt thereof,
(bp) Pyridinium, 4-[[[2-(benzoyloxy)ethyl]amino]carbonyl]-1-(2-ethoxy-2-oxoethyl)-, bromide or a pharmaceutically acceptable salt thereof,
(bq) Pyridinium, 1-(2-ethoxy-2-oxoethyl)-3-[(2-phenylhydrazino)carbonyl]-, bromide or a pharmaceutically acceptable salt thereof,
(br) Pyridinium, 3-[[2-[(4-methoxyphenyl)sulfonyl]hydrazino]carbonyl]-1-(2-oxo-2-phenylethyl)-, bromide or a pharmaceutically acceptable salt thereof,
(bs) Pyridinium, 4-[[[2-(benzoyloxy)ethyl]amino]carbonyl]-1-(2-oxo-2-phenylethyl)-, bromide or a pharmaceutically acceptable salt thereof, and
(bt) Pyridinium, 1-(2-ethoxy-2-oxoethyl)-4-[[2-(methylsulfonyl)hydrazino]carbonyl]-, bromide or a pharmaceutically acceptable salt thereof.

30. The process as claimed in claim 13, wherein the substituted pyridine is selected from the group consisting of:

N,N'-bis(nicotinyl)hydrazine,
3-[(2-pyridyl)hydrazinocarbonyl]pyridine,
3-[(2-methanesulfonyl)hydrazinocarbonyl]pyridine,
3-[(2-benzoyloxy)ethylaminocarbonyl]pyridine,
3-[(2-phenylsulfonyl)hydrazinocarbonyl]pyridine,
3-[(2-acetoxy)ethyloxycarbonyl]pyridine,
3-[(2-benzoyloxy)ethyloxycarbonyl]pyridine,
3-[(2-methoxy)ethyloxycarbonyl]pyridine,
3-[(2-phenylaminocarbonyl)hydrazinocarbonyl]pyridine,
3-[(2-acetoxy)ethylaminocarbonyl]pyridine,
3-[(2-(4-methylphenyl sulfonylhydrazinocarbonyl))] pyridine,
3-[(2-benzoyl)-hydrazino carbonyl]pyridine,
3-[(2-phenylmethane sulfonyl)hydrazino carbonyl]pyridine,
3-[(2-(3-cyclohexylpropanoyl)hydrazino carbonyl]pyridine,
3-[(2-methoxy)ethylaminocarbonyl]pyridine, and
3-[1-oxo-1-(2-methoxycarbonyl)pyridyl]hydrazino pyridine;

and said quaternizing agent is selected from the group consisting of:

2-bromoacetyl thiophene,
2-chloroacetyl thiopene,
phenacylbromide,
phenacylchloride,
2,4-dichloropheanacylbromide,
N-phenyl chloroacetamide,
N-cyclopropyl chloroacetamide,
ethylbromoacetate,
bromo acetylfuran,
N-isopropylchloroacetamide,
N-chloroacetyl-2-pyrrolidinone, and
chloroacetic acid.

31. Pyridinium, 3-[[2-(ethoxycarbonyl)hydrazino]carbonyl]-1-[2-oxo-2-(2-thienyl)ethyl]-, bromide or a pharmaceutically acceptable salt thereof.

32. A pharmaceutical composition comprising a pharmaceutically effective amount of the compound as claimed in claim 31 or pharmaceutically acceptable salt thereof in admixture with a pharmaceutically acceptable carrier, diluent, solvent or excepient.

33. The pharmaceutical composition as claimed in claim 32 in the form of an oral formulation.

34. The pharmaceutical composition as claimed in claim 32, wherein said acceptable carrier, diluent, solvent or excepient is selected from the group consisting of starch, lactose, polyvinyl pyrolidone (K-30), talc and magnesium stearate.

35. The pharmaceutical composition as claimed in claim 32, in the form of a parenteral formulation.

36. A method for preparation of a parenteral formulation as claimed in claim 35, which comprises dissolving pyridinium, 3-[[2-(ethoxycarbonyl)hydrazino]carbonyl]-1-[2-oxo-2-(2-thienyl)ethyl]-, bromide or a pharmaceutically acceptable salt thereof in polyethylene glycol 400 and diluting the solution so obtained with an isotonic solution or water to a desired concentration.

37. The pharmaceutical composition as claimed in claim 32 in the form of a lotion, oral rinse and toothpaste.

38. A method for treating a diabetic patient by breaking a preformed AGE, within said patient, which comprises, administering an effective amount of the compound as claimed in claim 31 or pharmaceutically acceptable salt thereof, either singly, or in combination with other drugs for antidiabetic therapy.

39. A method of preventing or treating diseases caused by diabetic and aging related complications including vascular and neuro-vascular complications which comprises administering to a patient in need thereof an effective amount of the compound as claimed in claim 31 or pharmaceutically acceptable salt thereof, either singly or in combination with a pharmaceutically acceptable carrier, diluent, solvent or excepient.

40. The method as claimed in claim 39, wherein the disease prevented or treated is a nephrological disorder, neurological disorder, atherosclerosis, retinal disorder, dermatological disorder, non-enzymatic browning of oral cavity, endothelial or other organ dysfunction and growth impairment.

41. The method as claimed in claim 39, wherein the disease prevented or treated is an inflammatory disorder, immunological disorder, or oxidative stress.

* * * * *